(12) United States Patent  
Criscuolo et al.

(10) Patent No.: US 8,485,414 B2  
(45) Date of Patent: *Jul. 16, 2013

(54) SURGICAL APPARATUS AND STRUCTURE FOR APPLYING SPRAYABLE WOUND TREATMENT MATERIAL

(75) Inventors: Christopher J. Criscuolo, Branford, CT (US); Michael J. Bettuchi, Middletown, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/533,041

(22) Filed: Jun. 26, 2012

(65) Prior Publication Data

US 2012/0265154 A1    Oct. 18, 2012

Related U.S. Application Data

(60) Continuation of application No. 12/751,285, filed on Mar. 31, 2010, now Pat. No. 8,225,981, which is a division of application No. 11/241,265, filed on Sep. 30, 2005, now Pat. No. 7,717,313.

(60) Provisional application No. 60/620,168, filed on Oct. 18, 2004, provisional application No. 60/620,151, filed on Oct. 18, 2004, provisional application No. 60/620,171, filed on Oct. 18, 2004, provisional application No. 60/620,150, filed on Oct. 18, 2004.

(51) Int. Cl.
*A61B 17/04*    (2006.01)
*A61B 17/10*    (2006.01)

(52) U.S. Cl.
USPC .................................. 227/179.1; 227/175.1

(58) Field of Classification Search
USPC ...................... 227/175.1–182.1, 19; 606/219
See application file for complete search history.

(56) References Cited

U.S. PATENT DOCUMENTS 3,079,606 A    3/1963    Bobrov et al.
3,490,675 A    1/1970    Green et al.
(Continued)

FOREIGN PATENT DOCUMENTS

EP    0 577 373    1/1994
JP    06327683    11/1994
(Continued)

OTHER PUBLICATIONS

International Search Report corresponding to European Application No. EP 05809831.0-1269 mailed May 14, 2012; 10 pages.

(Continued)

*Primary Examiner* — Robert Long

(57) ABSTRACT

According to an aspect of the present disclosure, an apparatus for forming an anastomosis between adjacent sections of tissue is provided. The apparatus includes a body portion; an actuation assembly operatively supported at a proximal end of the body portion; an anvil assembly movably mounted at the distal end of the body portion for movement toward and away from the body portion; an approximation assembly extending between the body portion and the anvil assembly for moving the anvil toward and away from the tubular body portion; a dispersion assembly operatively associated with the approximation assembly, the dispersion assembly including at least one angled surface defining at least one channel interposed between the anvil assembly and the body portion and being configured to dispense a fluid therefrom; and at least one conduit for conducting wound treatment material to the dispersion assembly.

20 Claims, 19 Drawing Sheets

U.S. PATENT DOCUMENTS

| | | |
|---|---|---|
| 3,499,591 A | 3/1970 | Green |
| 4,207,898 A | 6/1980 | Becht |
| 4,429,695 A | 2/1984 | Green |
| 4,603,693 A | 8/1986 | Conta et al. |
| 4,873,977 A | 10/1989 | Avant et al. |
| 5,065,929 A | 11/1991 | Schulze et al. |
| 5,156,613 A | 10/1992 | Sawyer |
| 5,156,614 A | 10/1992 | Green et al. |
| 5,205,459 A | 4/1993 | Brinkerhoff et al. |
| 5,254,113 A | 10/1993 | Wilk |
| 5,318,531 A | 6/1994 | Leone |
| 5,392,979 A | 2/1995 | Green et al. |
| 5,411,508 A | 5/1995 | Bessler et al. |
| 5,445,644 A | 8/1995 | Pietrafitta et al. |
| 5,465,896 A | 11/1995 | Allen et al. |
| 5,542,594 A | 8/1996 | McKean et al. |
| 5,554,119 A | 9/1996 | Harrison et al. |
| 5,611,775 A | 3/1997 | Machold et al. |
| 5,669,934 A | 9/1997 | Sawyer |
| 5,690,675 A | 11/1997 | Sawyer et al. |
| 5,735,833 A | 4/1998 | Olson |
| 5,749,895 A | 5/1998 | Sawyer et al. |
| 5,799,857 A | 9/1998 | Robertson et al. |
| 5,824,015 A | 10/1998 | Sawyer |
| 5,843,033 A | 12/1998 | Ropiak |
| 5,866,561 A | 2/1999 | Ungs |
| 5,895,412 A | 4/1999 | Tucker |
| 5,915,616 A | 6/1999 | Viola et al. |
| 5,931,165 A | 8/1999 | Reich et al. |
| 5,964,394 A | 10/1999 | Robertson |
| 6,032,849 A | 3/2000 | Mastri et al. |
| 6,045,560 A | 4/2000 | McKean et al. |
| 6,149,641 A | 11/2000 | Ungs |
| 6,165,201 A | 12/2000 | Sawhney |
| 6,179,862 B1 | 1/2001 | Sawhney |
| 6,228,051 B1 | 5/2001 | Trumbull |
| 6,287,323 B1 | 9/2001 | Hammerslag |
| 6,398,797 B2 | 6/2002 | Bombard et al. |
| 6,451,029 B1 | 9/2002 | Yeatman |
| 6,488,197 B1 | 12/2002 | Whitman |
| 6,491,201 B1 | 12/2002 | Whitman |
| 6,623,452 B2 | 9/2003 | Chien et al. |
| 6,681,979 B2 | 1/2004 | Whitman |
| 6,695,199 B2 | 2/2004 | Whitman |
| 7,141,055 B2 | 11/2006 | Abrams et al. |
| 7,238,195 B2 | 7/2007 | Viola |
| 7,455,682 B2 | 11/2008 | Viola |
| 7,699,204 B2 | 4/2010 | Viola |
| 7,823,592 B2 | 11/2010 | Bettuchi et al. |
| 7,845,536 B2 | 12/2010 | Viola et al. |
| 2001/0007069 A1 | 7/2001 | Bombard et al. |
| 2002/0010482 A1 | 1/2002 | Watt |
| 2002/0026159 A1 | 2/2002 | Zhu et al. |
| 2002/0049454 A1 | 4/2002 | Whitman et al. |
| 2002/0156150 A1 | 10/2002 | Williams et al. |
| 2002/0165562 A1 | 11/2002 | Grant et al. |
| 2002/0165563 A1 | 11/2002 | Grant et al. |
| 2002/0173558 A1 | 11/2002 | Williams et al. |
| 2003/0050590 A1 | 3/2003 | Kirsch |
| 2003/0073981 A1 | 4/2003 | Whitman et al. |
| 2003/0073982 A1 | 4/2003 | Whitman |
| 2003/0078597 A1 | 4/2003 | Blatter et al. |
| 2003/0089757 A1 | 5/2003 | Whitman |
| 2003/0111507 A1 | 6/2003 | Nunez |
| 2003/0236518 A1 | 12/2003 | Marchitto et al. |
| 2004/0059283 A1 | 3/2004 | Kirwan et al. |
| 2004/0092960 A1 | 5/2004 | Abrams et al. |
| 2004/0093029 A1 | 5/2004 | Zubik et al. |
| 2005/0038471 A1 | 2/2005 | Chan et al. |
| 2005/0043678 A1 | 2/2005 | Freyman et al. |
| 2005/0059996 A1* | 3/2005 | Bauman et al. ............... 606/215 |
| 2005/0059997 A1 | 3/2005 | Bauman et al. |
| 2005/0145671 A1 | 7/2005 | Viola |
| 2005/0230453 A1 | 10/2005 | Viola |
| 2006/0085032 A1 | 4/2006 | Viola |
| 2006/0085034 A1 | 4/2006 | Bettuchi |
| 2006/0108393 A1 | 5/2006 | Heinrich et al. |
| 2006/0135992 A1 | 6/2006 | Bettuchi et al. |
| 2006/0271104 A1 | 11/2006 | Viola et al. |
| 2007/0034666 A1 | 2/2007 | Holsten et al. |
| 2009/0078739 A1 | 3/2009 | Viola |
| 2010/0230466 A1 | 9/2010 | Criscuolo et al. |
| 2011/0036889 A1 | 2/2011 | Heinrich et al. |

FOREIGN PATENT DOCUMENTS

| | | |
|---|---|---|
| WO | WO 90/05489 | 5/1990 |
| WO | WO 00/56376 | 9/2000 |
| WO | WO 01/62158 | 8/2001 |
| WO | WO 01/62162 | 8/2001 |
| WO | WO 02/30297 | 4/2002 |
| WO | WO 03/088844 | 10/2003 |
| WO | WO 03/088845 A2 | 10/2003 |
| WO | WO 03/094743 | 11/2003 |
| WO | WO 03/094746 | 11/2003 |
| WO | WO 03/105698 | 12/2003 |

OTHER PUBLICATIONS

International Search Report from Application No. PCT/US05/37253 dated May 28, 2008.
European Search Report for Application EP 05022586.

* cited by examiner

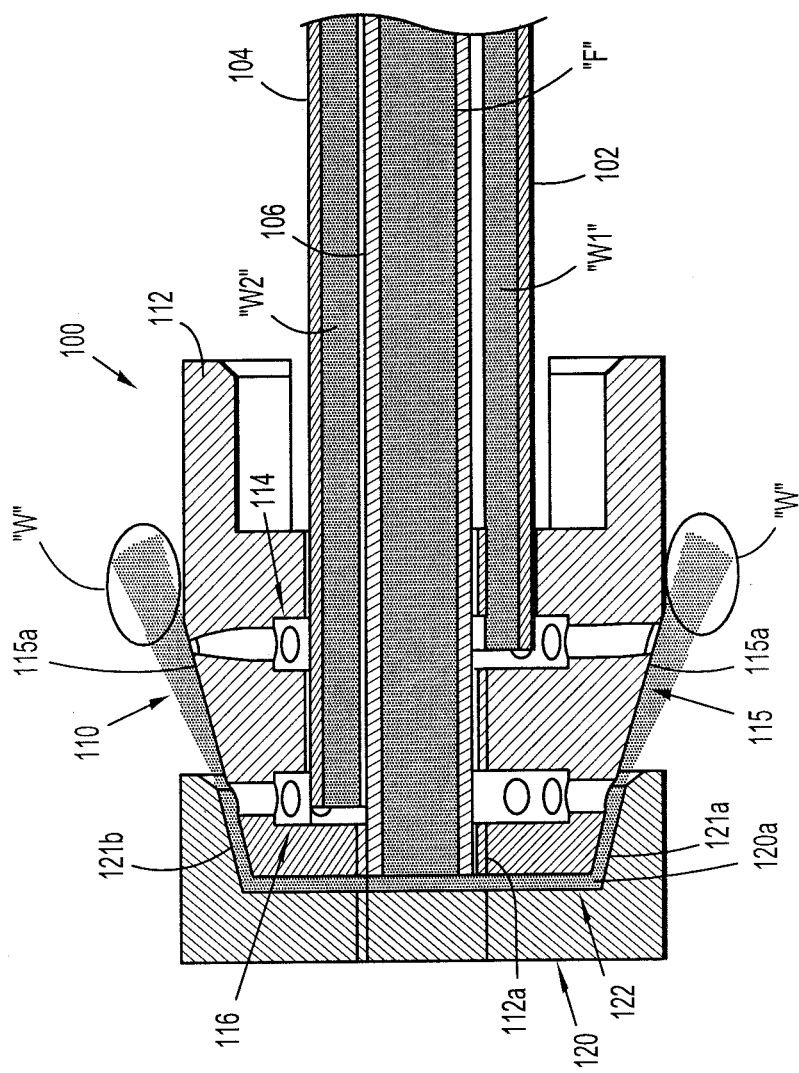
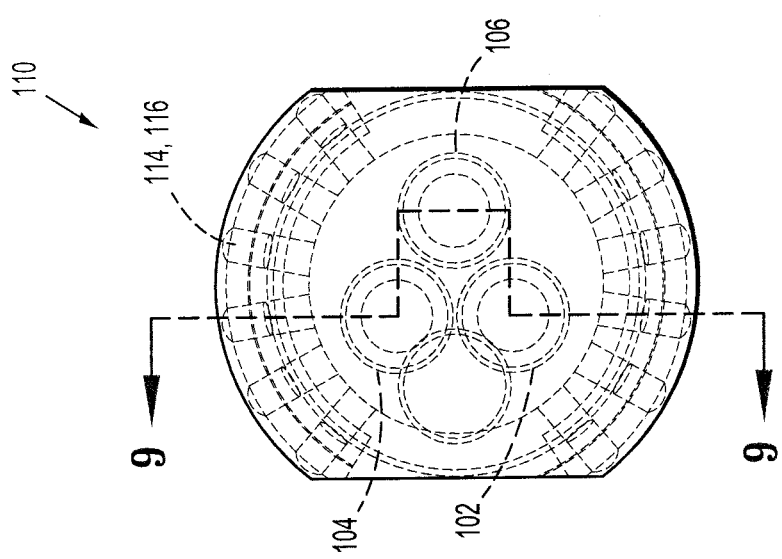
FIG. 9
FIG. 8

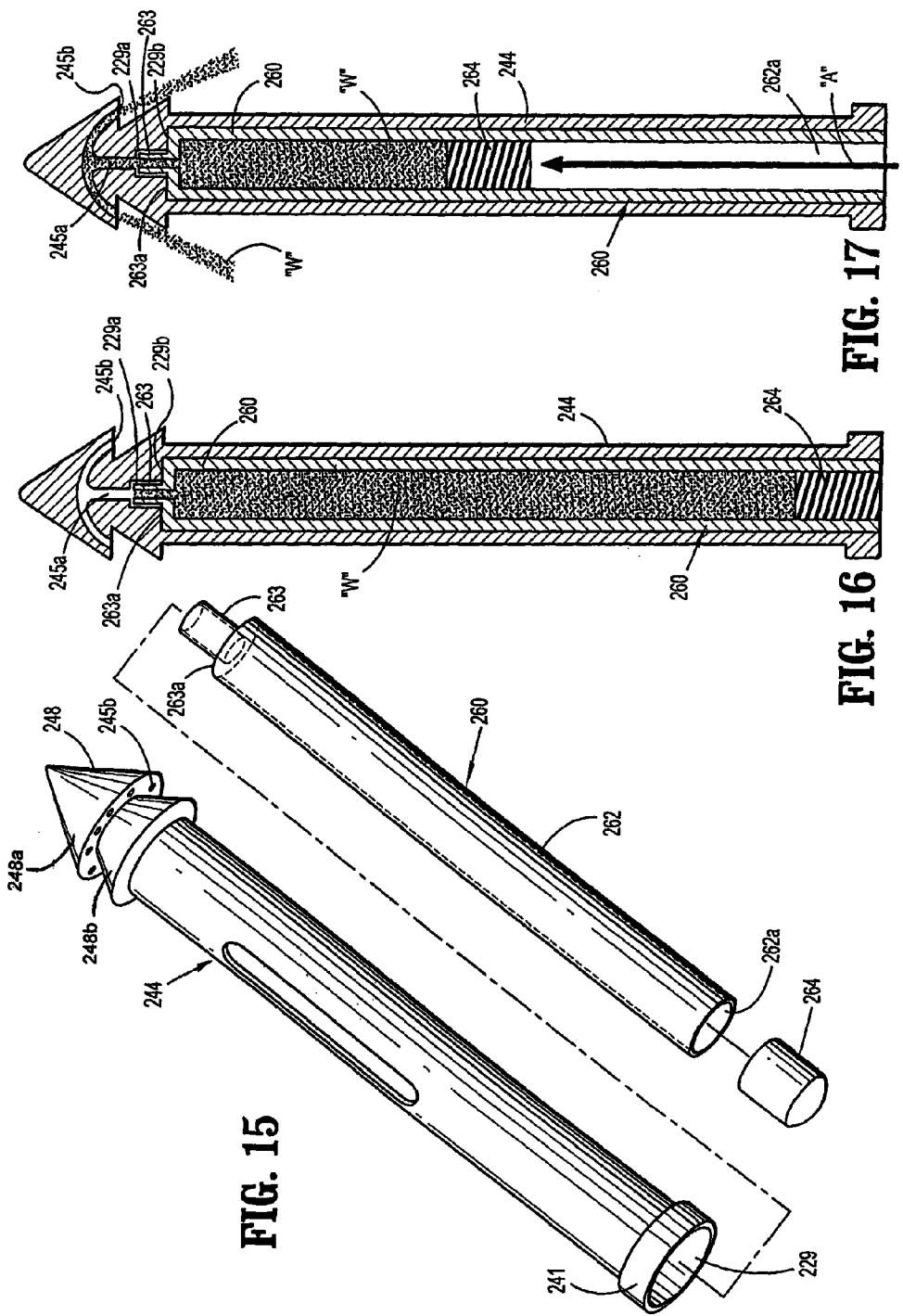

SURGICAL APPARATUS AND STRUCTURE FOR APPLYING SPRAYABLE WOUND TREATMENT MATERIAL

CROSS-REFERENCE TO RELATED APPLICATIONS

This application is a continuation of U.S. patent application Ser. No. 12/751,285 filed Mar. 31, 2010 now U.S. Pat. No. 8,225,981, which is a divisional of U.S. patent application Ser. No. 11/241,265 filed Sep. 30, 2005, now U.S. Pat. No. 7,717,313, which claims benefit of each of U.S. Provisional Application No. 60/620,168 filed Oct. 18, 2004, U.S. Provisional Application No. 60/620,151 filed Oct. 18, 2004, U.S. Provisional Application No. 60/620,171 filed Oct. 18, 2004, and U.S. Provisional Application No. 60/620,150 filed Oct. 18, 2004, the disclosures of each of the above-identified applications are hereby incorporated by reference in their entirety.

BACKGROUND

1. Technical Field

The present disclosure relates to surgical apparatus and methods for enhancing properties of tissue repaired or joined by surgical staples and, more particularly to surgical apparatus and structure configured to apply surgical mechanical fasteners and/or a non-mechanical biocompatible wound treatment material to enhance the properties of repaired or adjoined tissue at a target surgical site.

2. Discussion of Related Art

Throughout the years the medical field has utilized various techniques in an effort to join or bond body tissue together. Historically, suturing was the accepted technique for rejoining severed tissues and closing wounds. Suturing was historically achieved with a surgical needle and a suturing thread, and more recently, with a variety of polymeric or metallic staples, as will be discussed below. The intended function of sutures is to hold the edges of a wound or tissue against one another during the healing process so as to reduce discomfort, pain, scarring and the time required for healing.

Recently, many procedures which in the past required conventional suturing have been replaced by staple suturing which involves the application of the staples to the edges of the wound or tissue with the use of a surgical stapler. Surgical staplers have been developed for joining adjacent tissue, for providing hemostasis of adjacent tissue and for providing hemostasis in conjunction with cutting of adjacent tissue. Such surgical staplers include both linear and annular type configurations. A typical linear stapler and cutter includes parallel rows of staples with a slot for a cutting means to travel between the rows of staples.

Typical linear type staplers are disclosed in commonly assigned U.S. Pat. No. 6,045,560 to McKean et al., U.S. Pat. No. 6,032,849 to Mastri et al., and U.S. Pat. No. 5,964,394 to Robertson, the entire contents of each of which are incorporated herein by reference. A typical annular stapler and cutter, including a plurality of annular rows of staples, typically two, and an annular blade disposed internal of the rows of staples, is disclosed in commonly assigned U.S. Pat. Nos. 5,799,857 to Robertson et al. and 5,915,616 to Viola et al., the entire contents of each of which are incorporated herein by reference.

These types of surgical staplers secure adjoining body tissue for improved cutting, join layers of tissue to one another and provide hemostasis by applying parallel or annular rows of staples to surrounding tissue as the cutting means cuts between the parallel or annular rows. Accordingly, by enabling a surgeon to perform all of these tasks simultaneously, surgical staplers have been effective in decreasing the amount of time it takes to fasten tissue together. To even further enhance joining and hemostasis in instances where the stapler is used in highly vascularized tissue, surgical staplers with multiple rows of staples have been used with a high degree of success.

Other surgical procedures utilize pledgets, buttresses or other types of reinforcement materials and fabrics. These buttresses are typically placed over the tissue contacting surface of the anvil and/or the tissue contacting surface of the caitiidge of the surgical stapling instrument and secured against the target tissue during the firing of the surgical stapling instrument. Reference may be made to U.S. Pat. No. 5,542,594, the entire content of which is incorporated herein by reference, for a more detailed discussion of the use of buttresses in cooperation with surgical stapling instrument.

Still other surgical procedures involve the step of applying (e.g., by spraying, brushing, etc.) an adhesive material and/or a sealant material to the external surface of the target surgical site following the surgical stapling procedure.

Another procedure which has been developed includes the use of biological tissue adhesives have recently been developed for tissue repair and the creation of anastomoses. Generally, biological adhesives bond separated tissues together to aid in the healing process and to enhance the tissue strength. Such adhesives may be used instead of suturing and stapling for example in surgical procedures for the repair of tissue or the creation of anastomoses.

The application of a suitable biocompatible adhesive offers many advantages to the patient and the surgeon alike such as, for example, the avoidance of penetration of tissue by needles and/or staples, as well as the immediate sealing of the tissue being treated. Moreover, use of a biocompatible adhesive tends to minimize foreign body reaction and scarring. Despite these advantages, however, the weakness along the tissue seam remains as a primary disadvantage in the use of biocompatible adhesives.

Therefore, there is a need for surgical stapler instruments, for example surgical fasteners or staplers which reduce the trauma suffered by a patient, reduce the number of gaps between or at individual staple sites, reduce leakage of fluids, reduce bleeding, and/or which create a relatively strong bond between adjacent body tissues, e.g., along staple lines and tissue seams.

SUMMARY

The present disclosure relates to surgical instrument, structures, apparatus and methods for enhancing the properties of tissue to be repaired or joined.

According to an aspect of the present disclosure, an apparatus for forming an anastomosis between adjacent sections of tissue is provided. The apparatus includes a body portion; an actuation assembly operatively supported at a proximal end of the body portion; an anvil assembly movably mounted at the distal end of the body portion for movement toward and away from the body portion; an approximation assembly extending between the body portion and the anvil assembly for moving the anvil toward and away from the tubular body portion; a dispersion assembly operatively associated with the approximation assembly, the dispersion assembly including at least one angled surface defining at least one channel interposed between the anvil assembly and the body portion and being configured to dispense a fluid therefrom; and at least one conduit for conducting wound treatment material to the dispersion assembly.

The dispersion assembly may include a manifold. The manifold includes a plurality of ejection ports for dispensing the wound treatment material, wherein the channel directs the fluid across the ejection ports.

The ejection ports may include a plurality of first ejection ports formed therein for dispensing a first wound treatment material; and a plurality of second ejection ports formed therein for dispensing a second wound treatment material different from the first wound treatment material. The plurality of first ejection ports and the plurality of second ejection ports are both provided on opposed sides of the manifold. The plurality of proximal ejection ports and the plurality of distal ejection ports may be radially oriented.

The at least one conduit may include a first conduit having a distal end in fluid communication with the plurality of first ejection ports formed in the manifold; and a second conduit having a distal end in fluid communication with the plurality of second ejection ports formed in the manifold. It is envisioned that a distal end portion of the manifold may be tapered at an angle relative to a longitudinal axis of the body portion. It is further envisioned that the plurality of first ejection ports and the plurality of second ejection ports may be disposed in a distal end portion of the manifold.

The dispersion assembly may further include a cap operatively connected to a distal end of the manifold in such a manner so as to define a channel between an outer surface of the distal end portion of the manifold and an inner surface of the cap. The at least one ejection port may includes at least one third ejection port that communicates with the channel defined between the outer surface of the distal end portion of the manifold and the inner surface of the cap. The apparatus may further include a third conduit having a distal end in fluid communication with the third ejection port.

The first conduit may be connectable to a first fluid source, the second conduit may be connectable to a second fluid source, and the third conduit may be connectable to a third fluid source. The first fluid source may include a first part of a multi-part wound treatment material, and the second fluid source may include a second part of the multi-part wound treatment material. The multi-part wound treatment material is a sealant. The third source may include a fluid.

The cap and the distal end portion of the manifold may be shaped so that the channel directs the fluid in a substantially proximal direction. Accordingly, the fluid ejected from the channel causes the first and second parts of the multi-part wound treatment material to mix.

The actuation assembly may include at least one handle connected to the body portion. The approximation assembly may include a threaded rod member threadingly engaging the at least one handle; and a knob member operatively connected to a proximal end of the threaded rod member. The dispersion assembly may be operatively associated with the distal end of the threaded rod member. The threaded rod member may include windows formed on opposite sides thereof. The windows may be in registration with the at least one ejection port.

The distal end of the threaded rod member may include a connection member defining the windows. A distal end of the connection member may be configured to selectively engage a stem of an anvil assembly.

Accordingly to a further aspect of the present disclosure, a method of performing a surgical anastomosis procedure is provided. The method includes the steps of providing a surgical anastomosis apparatus having an anvil assembly movably mounted with respect to a body portion and a wound treatment material dispersion system disposed between the anvil assembly and the body portion for dispensing wound treatment material onto a target surgical site. The wound treatment material dispersion apparatus includes at least one ejection port configured to dispense at least one fluid; and at least one conduit for conducting wound treatment material to the wound treatment material dispersion apparatus.

The method further includes the steps of disposing an anvil assembly into a first intestinal section and securing the first intestinal section to the anvil assembly; disposing the body portion into a second intestinal section and securing the second intestinal section to the body portion; actuating the wound treatment material dispersion apparatus to dispense wound treatment material onto at least one of the first and the second intestinal sections; and approximating the anvil assembly toward the tubular body portion.

The method further includes the steps of dispensing a first part of a multi-part wound treatment material from a first set of ejection ports formed in the wound treatment material dispersion apparatus; and dispensing a second part of the multi-part wound treatment material from a second set of ejection ports formed in the wound treatment material dispersion apparatus.

The method further includes the step of mixing the first and second part of the multi-part wound treatment material. It is envisioned that the first and second parts of the multi-part wound treatment material are dispensed in a radially outward direction.

The method may further include the step of dispensing a fluid from the wound treatment material dispersion apparatus, in a direction transverse to the paths of dispersion of the first and second parts of the wound treatment material. It is contemplated that the fluid may be dispensed from the wound treatment material dispersion apparatus in a substantially proximal direction.

The method may further include the steps of ejecting a first fluid from a proximal set of ejection ports; and ejecting a second fluid from a distal set of ejection ports.

The method may still further include the steps of delivering the first fluid through a first conduit to the first set of ejection ports, from a first source of the first fluid; and delivering the second fluid through a second conduit to the second set of ejection ports from a second source of a second fluid.

It is envisioned that the multi-part wound treatment material may be selected from the group consisting of a two-part bio-adhesive and a two-part sealant.

The approximation assembly may include an inner rod member defining a lumen therethrough; a threaded rod member operatively associated with a proximal end of the inner rod member, wherein the treaded rod member threadingly engages the fixed handle member; a knob member operatively connected to a proximal end of the threaded rod member; and a connection member operatively connected proximate to a distal end of the inner rod member.

The wound treatment material dispersion apparatus may be operatively associated with the distal end of the inner rod member. The connection member may include windows formed on opposite sides thereof. The windows of the connection member may be in registration with the plurality of proximal ejection ports and the plurality of distal ejection ports of the manifold.

According to an aspect of the present disclosure, a circular surgical stapling apparatus is provided. The surgical stapling apparatus includes a tubular body portion having an actuator; a staple pusher member operatively disposed at a distal end of the tubular body portion and being operatively connected to the actuator for expelling an annular array of staples from the tubular body portion; an anvil assembly movably mounted at the distal end of the tubular body portion for movement toward and away from the tubular body portion; an approximation assembly extending between the tubular body portion and the anvil assembly for moving the anvil toward and away from the tubular body portion; a nozzle operatively associated with the approximation assembly, the nozzle including at least one ejection port disposed between the anvil assembly and the tubular body portion and being configured to dispense at least one fluid; and at least one conduit for conducting wound treatment material to the nozzle.

The nozzle may include a manifold. The manifold includes a plurality of first ejection ports formed therein for dispensing a first wound treatment material; and a plurality of second ejection ports formed therein for dispensing a second wound treatment material different from the first wound treatment material. The plurality of first ejection ports and the plurality of second ejection ports may both be provided on opposed sides of the manifold. The plurality of proximal ejection ports and the plurality of distal ejection ports may be radially oriented.

The at least one conduit may include a first conduit having a distal end in fluid communication with the plurality of first ejection ports formed in the manifold; and a second conduit having a distal end in fluid communication with the plurality of second ejection ports formed in the manifold. A distal end portion of the manifold may be tapered at an angle relative to a longitudinal axis, and the plurality of first ejection ports and the plurality of second ejection ports may be disposed in the distal end portion of the manifold.

The nozzle further includes a cap operatively connected to a distal end of the manifold in such a manner so as to define a channel between an outer surface of the distal end portion of the manifold and an inner surface of the cap. The at least one ejection port may include at least one third ejection port that communicates with the channel.

The apparatus may further include a third conduit having a distal end in fluid communication with the third ejection port. Accordingly, the first conduit may be connectable to a first fluid source, the second conduit may be connectable to a second fluid source, and the third conduit may be connectable to a third fluid source. The first fluid source may include a first part of a two-part wound treatment material, and the second source may include a second part of the two-part wound treatment material. The two-part wound treatment material may be a bio-adhesive. The third fluid source may include a compressed fluid.

The cap and the distal end portion of the manifold may be shaped so that the channel directs the fluid into a substantially proximal direction. In use, the fluid ejected from the channel causes the first and second parts of the two-part wound treatment material to mix.

The actuator includes at least one handle connected to the tubular body portion. The approximation assembly includes a threaded rod member threadingly engaging the at least one handle; and a knob member operatively connected to a proximal end of the threaded rod member. The nozzle of the wound treatment material dispersion system may be operatively associated with the distal end of the threaded rod member. The threaded rod member may include windows formed on opposite sides thereof. The windows may be in registration with the at least one ejection port. The distal end of the threaded rod member may include a connection member defining the windows, and a distal end of the connection member may be configured to selectively engage a stem of an anvil assembly.

According to another aspect of the present disclosure, a method of performing a surgical anastomosis procedure is provided. The method includes the steps of providing a circular surgical stapling apparatus having an anvil assembly movably mounted with respect to a tubular body portion and a wound treatment material dispersion system for dispensing wound treatment material onto a target surgical site. The wound treatment material dispersion system includes a nozzle disposed between the anvil assembly and the tubular body portion, the nozzle including at least one ejection port configured to dispense at least one fluid; and at least one conduit for conducting wound treatment material to the nozzle.

The method further includes the steps of disposing an anvil assembly into a first intestinal section; disposing a distal end portion of the surgical stapling apparatus into a second intestinal section; actuating the wound treatment material dispersion system to dispense wound treatment material onto at least one of the first and the second intestinal sections; and approximating the anvil assembly toward the tubular body portion.

The method may further include the steps of dispensing a first part of a two-part wound treatment material from a first set of ejection ports formed in the nozzle of the wound treatment material dispersion system; and dispensing a second part of the two-part wound treatment material from a second set of ejection ports formed in the nozzle of the wound treatment material dispersion system. The method may further include the step of mixing the first and second part of the two-part wound treatment material. The first and second parts of the two-part wound treatment material may be dispensed in a radially outward direction.

The method ma further include the step of dispensing a fluid from the nozzle of the wound treatment material dispersion system, in a direction transverse to the paths of dispersion of the first and second parts of the wound treatment material. The fluid may be dispensed from the nozzle in a substantially proximal direction.

The method may further include the steps of ejecting a first fluid from a proximal set of ejection ports; and ejecting a second fluid from a distal set of ejection ports. The method may further include the steps of delivering the first fluid through a first conduit to the first set of ejection ports, from a first source of the first fluid; and delivering the second fluid through a second conduit to the second set of ejection ports from a second source of a second fluid.

The two-part wound treatment material may be selected from the group consisting of a two-part bio-adhesive and a two-part sealant.

The approximation assembly may include an inner rod member defining a lumen therethrough; a threaded rod member operatively associated with a proximal end of the inner rod member, wherein the treaded rod member threadingly engages the fixed handle member; a knob member operatively connected to a proximal end of the threaded rod member; and a connection member operatively connected proximate to a distal end of the inner rod member. The nozzle of the wound treatment material dispersion system may be operatively associated with the distal end of the inner rod member.

The connection member may include windows formed on opposite sides thereof. The windows of the connection member may be in registration with the plurality of proximal ejection ports and the plurality of distal ejection ports of the manifold.

According to another aspect of the present disclosure, a surgical stapling apparatus, for dispensing wound treatment material to a target surgical site is provided. The apparatus includes a handle assembly; at least one pivotable actuating handle member connected to the handle assembly; a tubular body portion extending from the handle assembly; an anvil assembly including a stem and an anvil member supported on one end of the stem; a staple pusher member operatively supported on a distal end of the tubular body portion; connection means operatively disposed within the tubular body portion, the connection means being configured and adapted to operatively engage a second end of the stem; and an ampoule operatively disposed within the connection means. The ampoule contains a quantity of wound treatment material therein, and wherein during a surgical procedure, the wound treatment material is dispensed from the ampoule.

The ampoule may include a body portion defining a lumen for retaining the wound treatment material, and a plunger slidably disposed within the lumen. Accordingly, in use, as the plunger is axially displaced through the lumen, the wound treatment material contained therein is dispensed from an aperture formed in the body portion.

The connection means may include a trocar defining a cavity therein configured and dimensioned to receive the ampoule therein. The trocar defines at least one port in fluid communication with the aperture of the body portion of the ampoule. Accordingly, in use, as the wound treatment material is dispensed from the aperture of the body portion the wound treatment material is conducted through the at least one port of the trocar. Each port may be angled in a proximal direction.

The surgical stapling apparatus may further include a drive cable extending through the surgical stapling apparatus and engaging the plunger of the ampoule. In use, movement of the drive cable in a distal direction results in movement of the plunger in the distal direction to dispense the wound treatment material therefrom.

According to yet another aspect of the present disclosure, a surgical stapling apparatus for applying an annular array of staples, and a wound treatment material or at least one component of a wound treatment material is provided. The surgical stapling apparatus includes an anvil member positionable on a distal end of the stapling apparatus, the anvil member including an anvil stem adapted for connecting the anvil member to the distal end of the stapling apparatus, the anvil stem including a lumen extending therethrough, and at least one hole formed in an outer surface thereof and in fluid communication with the lumen; and a fastener assembly positioned adjacent a distal end of the stapling apparatus, the fastener assembly and anvil member being juxtaposable relative to each other. The fastener assembly includes a plurality of surgical staples individually disposed within staple slots provided in the fastener assembly; and a staple pusher member for firing the surgical staples from the individual staple slots and against the anvil member. The surgical stapler apparatus further includes a wound treatment material applicator assembly operatively associated with the stapler apparatus.

The applicator assembly includes at least one reservoir for storing a wound treatment material or at least one component of a wound treatment material; and a conduit system providing fluid communication between the at least one reservoir and the anvil stem of the anvil member, wherein the wound treatment material or the at least one component thereof flows from the at least one reservoir through the conduit system, the lumen of the anvil stem and dispenses out through the at least one hole formed in the anvil stem to an area substantially between the anvil member and the fastener assembly.

The conduit system may include a connection means defining a bore therethrough, wherein the connection means is adapted to engage the anvil stem of the anvil member such that the bore thereof is in fluid communication with the lumen of the anvil stem.

The at least one reservoir may be compressible. The at least one reservoir may be compressed before, during or after firing of the surgical stapling apparatus to expel the wound treatment material therefrom. The surgical stapling apparatus further includes a wound treatment material contained within the at least one reservoir.

The surgical stapling apparatus may further include a tubular body portion, wherein the fastener assembly is disposed at a distal end of the body portion; and means for actuating the fastener assembly to expel the annular array of staples therefrom.

The anvil member may be disposed at a distal end of the body portion and positioned opposite the fastener assembly. The anvil member may be adapted to clinch the staples in tissue upon expulsion of the staples.

The surgical stapling apparatus may further include means for advancing at least one of the staple pusher member and the anvil member from an extended position away from the other of the members to a position adjacent the other member. The surgical stapling apparatus may still further include a flexible member positioned coaxially within the tubular body portion, the flexible member being operatively coupled at a proximal end to the advancing means and at a distal end to the at least one member. The fastener assembly may be positioned on the distal end of the tubular body portion, and the advancing means may move the anvil member from the extended position away from the staple pusher member to the position adjacent the fastener assembly.

The advancing means may include a grip member positioned at a proximal end of the apparatus. The conduit system may include a connection means defining a bore therethrough. The connection means may be adapted to engage the anvil stem of the anvil member such that the bore thereof is in fluid communication with the lumen of the anvil stem.

It is envisioned that the at least one reservoir is compressible. The at least one reservoir may be compressed before, during or after firing of the surgical stapling apparatus to expel the wound treatment material therefrom. The surgical stapling apparatus may further include a wound treatment material contained within the at least one reservoir. The reservoir is desirably disposed between the actuating means and the grip member. Accordingly, movement of the actuating means toward the grip member results in the compression of the reservoir.

BRIEF DESCRIPTION OF THE DRAWINGS

The foregoing features of the present disclosure will become more readily apparent and may be understood by referring to the following detailed description of an illustrated embodiment of a surgical instrument, apparatus or structure, taken in conjunction with the accompanying drawings, in which:

FIG. 8 is a distal end view of the sprayer tip assembly of FIG. 7;

FIG. 9 is a cross-sectional view of the sprayer tip assembly of FIGS. 7 and 8 as taken through 9-9 of FIG. 8;

FIG. 15 is a perspective view of schematic illustration of a wound treatment material dispensing system according to the present disclosure;

FIG. 16 is a longitudinal cross-sectional view of the wound treatment material dispensing system of FIG. 15, with a plunger thereof in a first position;

FIG. 17 is a longitudinal cross-sectional view of the wound treatment material dispensing system of FIGS. 15 and 16, with the plunger thereof in a second position and illustrating the dispensing of wound treatment material therefrom;

DETAILED DESCRIPTION OF THE EMBODIMENT

Figure 1:
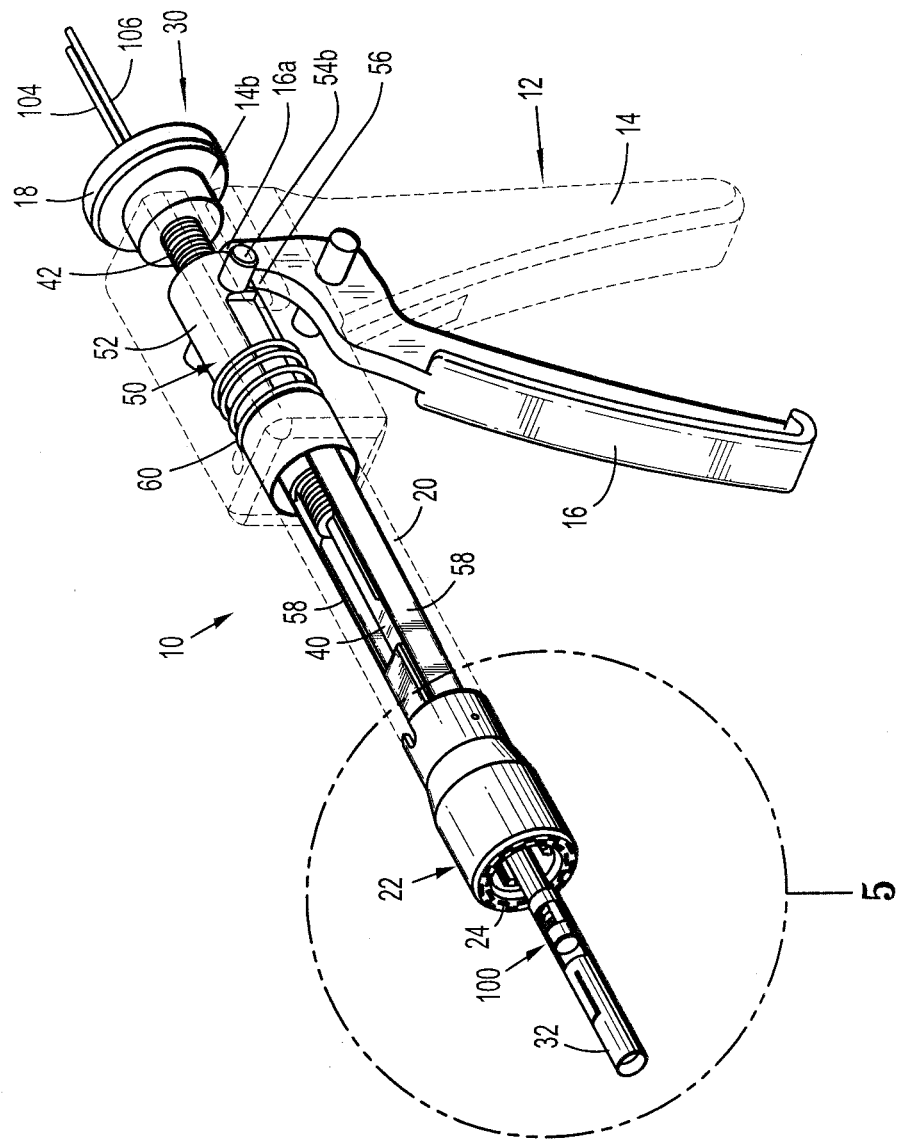
FIG. 1 illustrates a perspective view of a surgical stapling apparatus according to an embodiment of the present disclosure.

Embodiments of the presently disclosed surgical stapling apparatus will now be described in detail with reference to the drawing figures wherein like reference numerals identify similar or identical elements. As used herein and as is traditional, the term "distal" refers to that portion which is furthest from the user while the term "proximal" refers to that portion which is closer to the user.

Figure 2:
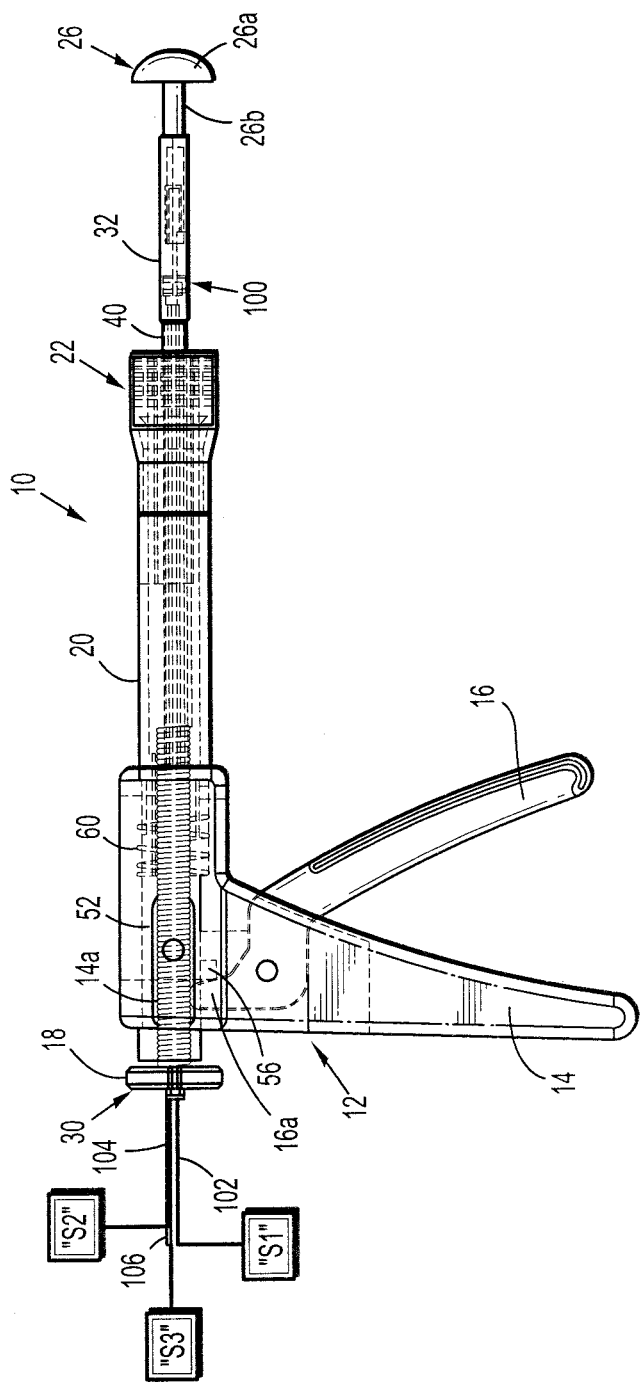
FIG. 2 is a longitudinal cross-sectional view of the surgical stapling apparatus of FIG. 1.

With reference to FIGS. 1 and 2, surgical stapling apparatus 10 includes a tubular body portion 20 and an actuator that desirably comprises an actuator or handle assembly 12. In the embodiment shown, handle assembly 12 has a fixed handle member 14 and a pivotable handle member 16. In certain embodiments, tubular body portion 20 is desirably constructed so as to have a straight shape along at least a portion of its length. It is also envisioned that tubular body portion 20 is constructed so as to be curved along at least a portion of its length, or in other embodiments, tubular body portion 20 may be flexible to bend to any configuration. Body portion 20 houses a staple pusher member 22. Body portion 20 includes an annular array of staple pockets 24 (best seen in FIG. 5), which may be housed in a staple cartridge, for retaining staples (not shown) therein.

Staple pusher member 22 includes a member movably mounted in body portion 20, as is known in the art. Staple pusher member 22 may include fingers extending axially in alignment with the staples in the cartridge. The body portion 20 also desirably houses a blade or blades, preferably having an annular shape. Positionable opposite body portion 20 is an anvil assembly 26 including an anvil member 26a and a stem 26b extending from the anvil member 26a which is detachably connected to connection member 32 of approximation assembly 30. An exemplary anvil assembly 26 for use with stapling apparatus 10 is disclosed in certain embodiments of commonly assigned U.S. Pat. No. 5,119,983, issued Jun. 9, 1992, and U.S. Pat. No. 5,718,360, which are hereby incorporated in their entirety herein by reference. In other embodiments, anvil assembly 26 is not detachable from connection member 32.

The anvil assembly 26 is positionable opposite the tubular body portion 20 for movement towards and away from tubular body portion 20. However, it is of course contemplated that anvil assembly 26 may be positioned at the distal end of tubular body portion 20 and the staple pusher member 22 and the array of staples may be positioned opposite anvil assembly 26 for movement towards and away from anvil assembly 26. Such a construction is to be considered within the scope of the present disclosure.

Figure 3:
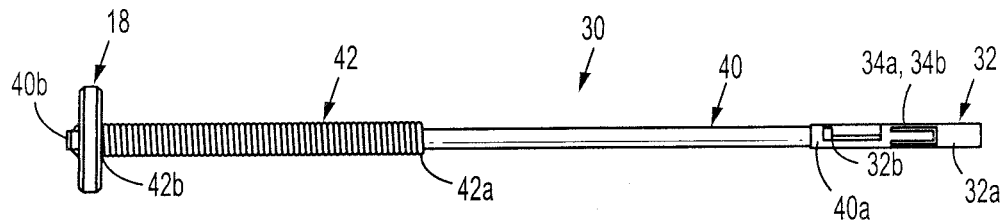
FIG. 3 is a side view of an approximation assembly of the surgical stapling apparatus of FIGS. 1 and 2.

The stapling apparatus 10 includes an approximation assembly 30 for moving the anvil assembly 26 toward and away from tubular body portion 20. As seen in FIG. 3, approximation assembly 30 includes a connection member 32, an inner rod member 40, a threaded rod member 42, and a knob member 18. Connection member 32 includes a distal end 32a configured and adapted to releasably engage stem 26b (see FIG. 2) of an anvil assembly 26. The connection member 32 may be integrally formed with inner rod member 40 or, as shown in FIG. 3, may have a proximal end 32b operatively connected to a distal end 40a of inner rod member 40. Proximal portion 32b of connection member 32 includes windows 34a, 34b formed on either side thereof. Inner rod member 40 includes a proximal end 40b which may be operatively connected to a distal end 42a of threaded rod member 42 or, in the alternative, extends completely through threaded rod member 42. Knob member 18 is desirably secured to a proximal end 42b of threaded rod member 42.

Figure 4:
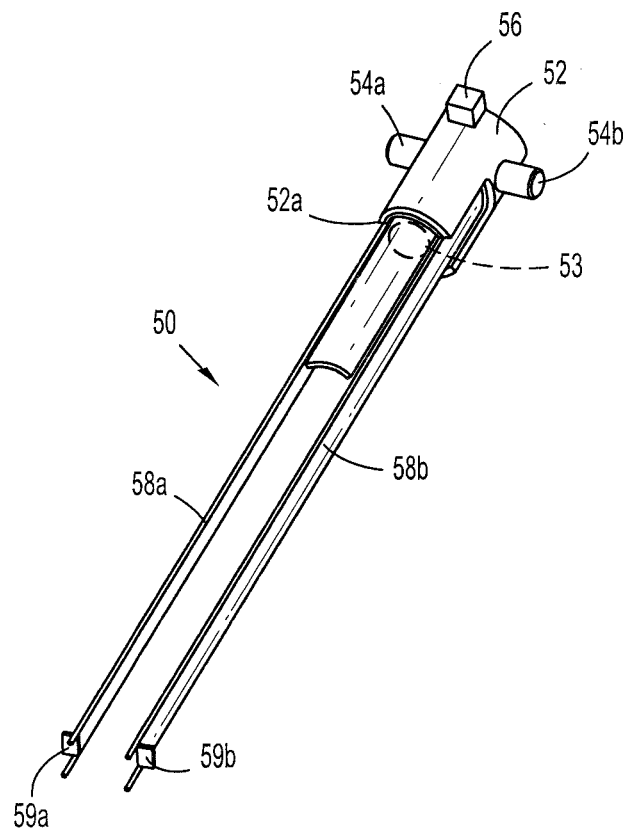
FIG. 4 is a perspective view of a drive assembly of the surgical stapling apparatus of FIGS. 1-3.

As seen in FIG. 4, the surgical stapling apparatus 10 includes a drive assembly 50. Drive assembly 50 includes a bushing 52 defining a lumen 53 (shown in phantom) therethrough, a pair of opposed stems 54a, 54b extending radially from bushing 52, and a nub 56 extending radially from bushing 52. Desirably, stems 54a and 54b slidably engage respective elongate slots 14a, 14b formed in fixed handle member 14 (see FIGS. 1 and 2). Drive assembly 50 further includes a pair of drive arms 58a, 58b operatively connected to bushing 52 and extending axially therefrom. Threaded rod member 42 and/or inner rod member 40 of approximation assembly 30 slidably extends through lumen 53 of bushing 52.

As will be described in greater detail below, a stem 16a extending from a proximal end portion of actuating handle member 16 operatively engages nub 56 of bushing 52. This is best seen in FIGS. 1 and 2. In this manner, as actuating handle member 16 is squeezed or approximated toward fixed handle member 14, stem 16a of actuating handle member 16 engages or presses against nub 56 of bushing 52 to move or force drive assembly 50 in a distal direction. Drive assembly 50 is maintained in a substantially linear path due to the sliding engagement of opposed stems 54a and 54b of bushing 52 in elongate slots 14a, 14b of fixed handle member 14. Movement of drive assembly 50 in a distal direction causes a distal ends 59a, 59b of drive arms 58a, 58b to actuate staple pusher member 22 to thereby drive out the staples retained therein. Other mechanisms for driving staples may be used, such as hydraulics, linkages, cables, etc.

Desirably, as seen in FIGS. 1 and 2, surgical stapling apparatus 10 desirably includes a biasing member 60 for returning drive assembly 50 and/or actuating handle member 16 to the pre-actuated or pre-fired position. Biasing member 60 may include a compression spring disposed between a proximal facing surface of fixed handle member 14 and a distal facing surface 52a (see FIG. 4) of bushing 52. In this manner, when actuating handle member 16 is squeezed, bushing 52 is moved distally and biasing member 60 is compressed or biased. Accordingly, when actuating handle member 16 is released, biasing member 60 expands and moves bushing 52 in a proximal direction which in turn returns actuating handle member 16 to an un-squeezed condition.

Figure 11:
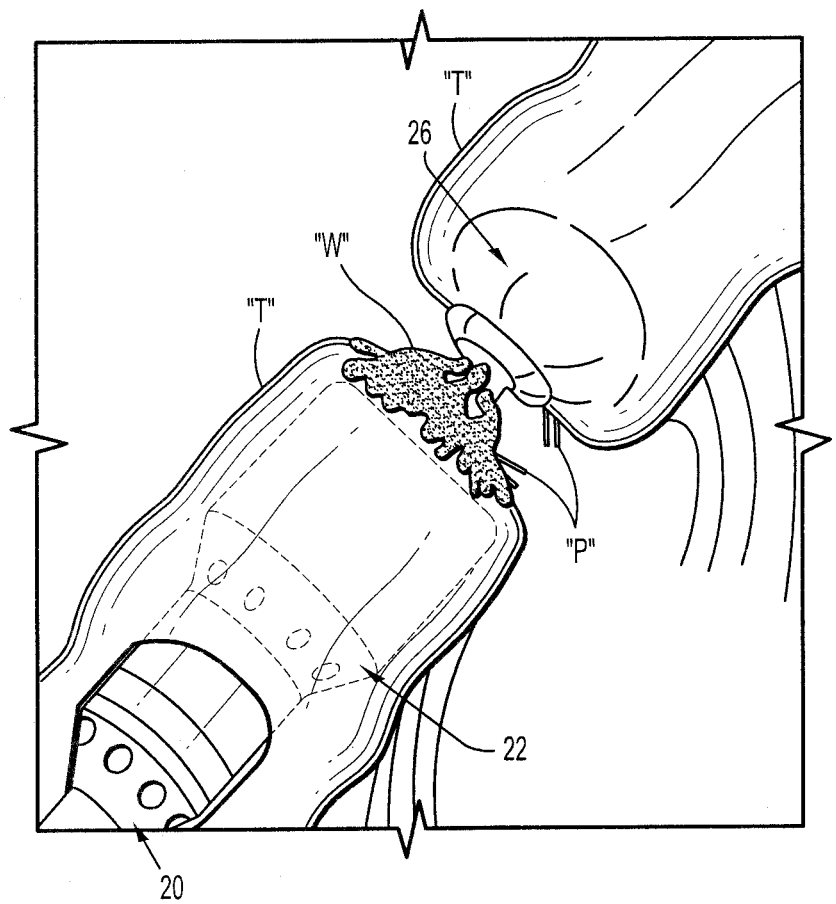
FIG. 11 is a schematic perspective view of the distal end of the surgical stapling apparatus of FIGS. 1-10 illustrating the dispensing of wound treatment material therefrom.

In a typical method of operation, apparatus 10 is positioned within a tubular organ in the body of the patient and the ends of the organ to be joined are positioned in the gap between tubular body portion 20 and anvil assembly 26. As is conventional, the ends of the organ may be secured over anvil assembly 26 and tubular body portion 20 by a purse string suture prior to approximation of anvil assembly 26 in relation to tubular body portion 20 (see FIG. 11). In embodiments having a detachable anvil assembly, the tubular body portion 20 and anvil assembly 26 are separately positioned within the tubular organ ends and reconnected after the purse string sutures are applied.

In order to approximate anvil assembly 26 towards tubular body portion 20, knob member 18 is rotated to displace approximation assembly 30 in a proximal direction relative to handle assembly 12. This draws anvil assembly 26 into position adjacent tubular body portion 20 and locates the ends of the tissue between these two members. Once the proper distance is set between anvil assembly 26 and tubular body portion 20, actuating handle member 16 is pivoted or squeezed to move drive assembly 50 in a distal direction, actuate staple pusher member 22 and drive the staples through the tissue. The staples are driven against anvil member 26a of anvil assembly 26 and the tissue located inwardly of the staples is desirably cut with a blade, to complete the circular anastomosis of the tubular organ.

Figure 5:
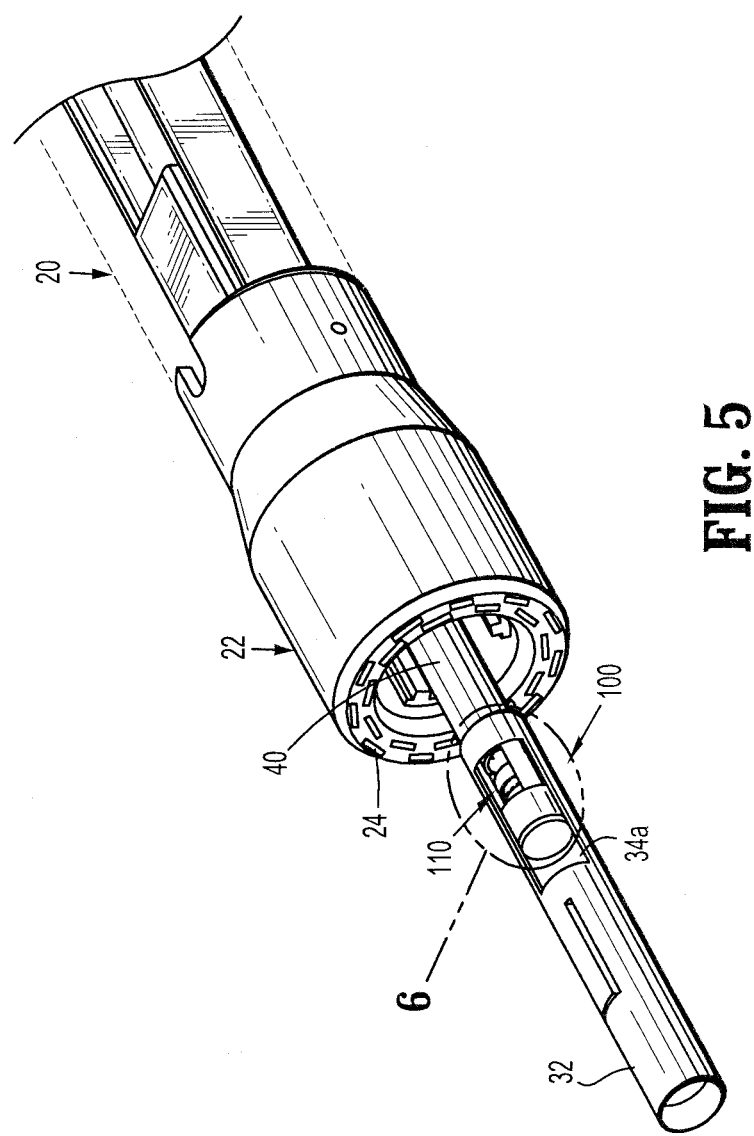
FIG. 5 is an enlarged perspective view of the indicated area of detail of FIG. 1.
Figure 6:
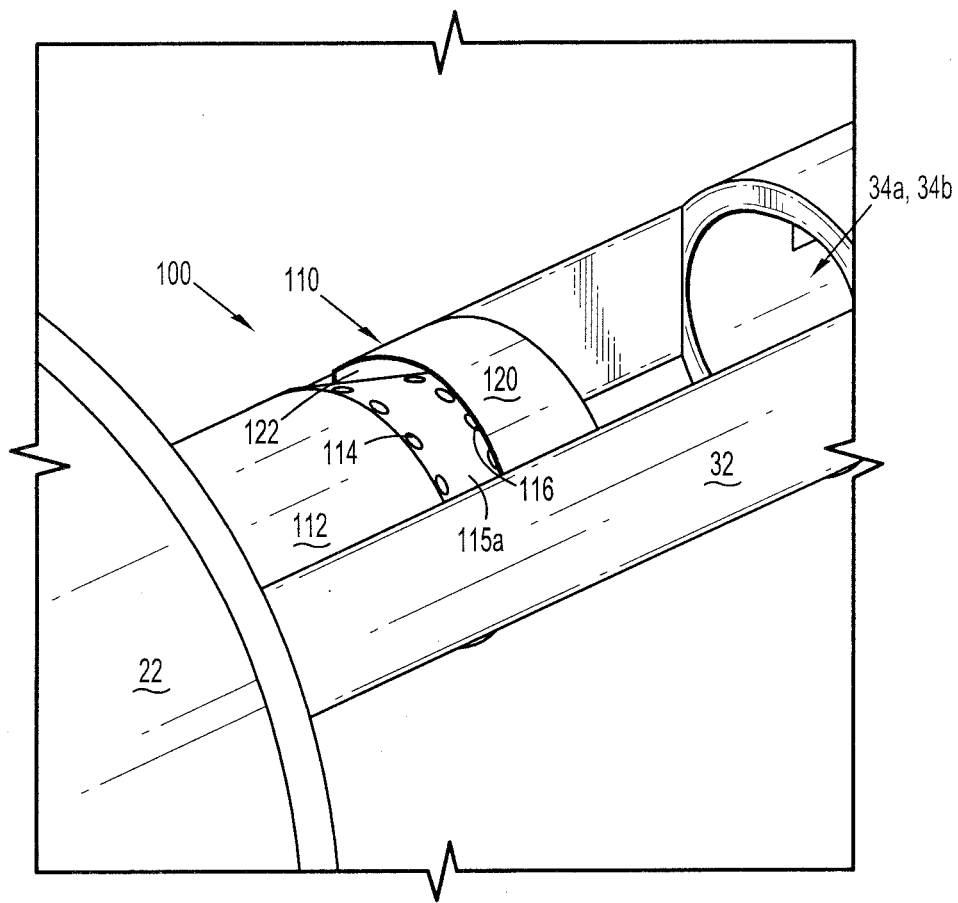
FIG. 6 is an enlarged perspective view of the indicated area of detail of FIG. 5.
Figure 7:
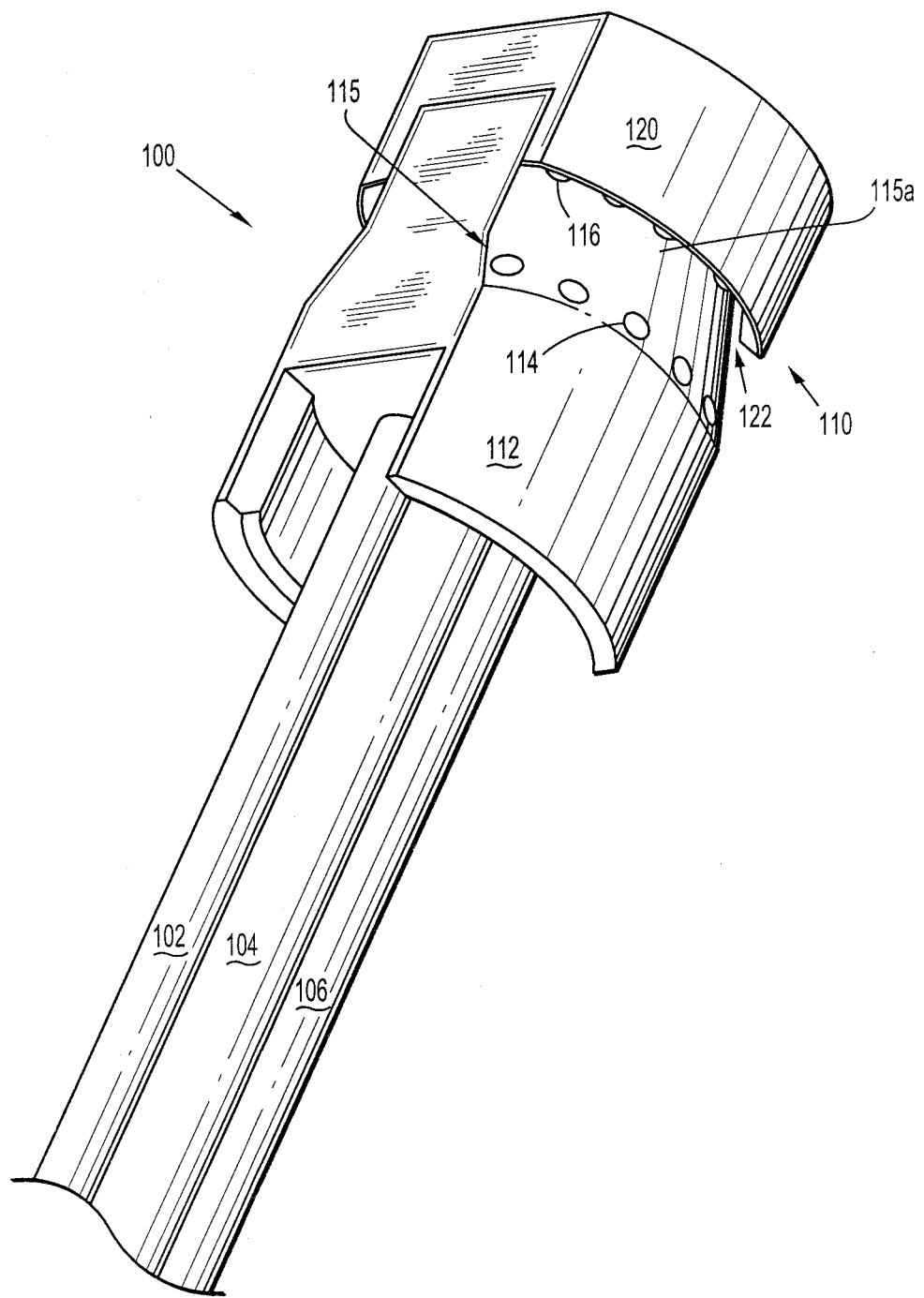
FIG. 7 is a perspective view of a sprayer tip assembly of the surgical stapling apparatus of FIGS. 1-6.

Turning now to FIGS. 5-9, surgical stapling apparatus 10 includes a wound treatment material dispersion system 100 configured to disperse (e.g., spray, eject, squeeze, dispense, etc.) wound treatment material "W" onto a surface of tissue "T". Wound treatment material dispersion system 100 includes at least one conduit, such as first conduit 102, second conduit 104, and third conduit 106 (FIGS. 1, 2 and 7-9), for transmitting fluid through stapling apparatus 10 to a dispersion head or nozzle 110. Desirably, nozzle 110 is operatively associated with approximation assembly 30. For example, as shown in FIGS. 5 and 6, nozzle 110 is disposed in connection member 32. Nozzle 110 includes a manifold 112 configured and adapted to receive and dispense the fluid communicated thereto from conduits 102, 104 and 106.

Conduits 102, 104 and 106 extend through the lumen of inner rod member 40 and extend out a proximal end of surgical stapling apparatus 10. A proximal end of each conduit 102, 104 and 106 is desirably fluidly connected to at least one source of fluid. In certain preferred embodiments, each conduit 102, 104 and 106 is fluidly connected to a respective source of fluid "S1, S2 and S3" (see FIG. 2). Source of fluid "S1" is connected to conduit 102, source of fluid "S2" is connected to conduit 104, and source of fluid "S3" is connected to conduit 106. In other embodiments, fewer or more than three conduits and/or sources are used. In other embodiments, one or more of the sources of fluid are housed within the stationary handle 14 or tubular body portion 20. The source or sources of fluid may also comprise a separate reservoir connectable to the stationary handle 14 or tubular body portion 20.

Manifold 112 includes a plurality of proximal ejection ports 114 formed preferably on at least two opposed sides of manifold 112. A distal end of first conduit 102 is in fluid communication with the proximal array of ejection ports 114. In this manner, as will be described in greater detail below, fluid transmitted from first source "S1" of fluid, through first conduit 102, is dispensable or ejectable from the proximal array of ejection ports 114.

Manifold 112 further includes a plurality of distal ejection ports 116 formed preferably on at least two opposed sides of manifold 112, adjacent the proximal ejection ports 114. A distal end of second conduit 104 is in fluid communication with the distal array of ejection ports 116. In this manner, as will be described in greater detail below, fluid transmitted from second source "S2" of fluid, is conducted through second conduit 104, and dispensable or ejectable from the distal array of ejection ports 116. In other embodiments, one or more sources of fluid are in communication with the same ejection port or portion.

A distal end portion 115 of manifold 112 is angled to define a pair of angled surfaces 115a, as best seen in FIG. 9. Each angled surface 115a of distal end portion 115 of manifold 112 is desirably angled at from about 1° to about 90° relative to a longitudinal "X" axis, desirably angled at about 15° relative to the longitudinal "X" axis.

Nozzle 110 further includes a cap 120 operatively connected to the distal end of manifold 112. Cap 120 is operatively connected to manifold 112 in such a manner so as to define a channel or space 122 between a proximal facing inner surface 120a of cap 120 and a distal-most surface 112a of manifold 112. Additionally, cap 120 includes a pair of angled inner surfaces 121a, 121b extending proximally from inner surface 120a. Angled inner surfaces 121a, 121b complement the pair of angled surfaces 115a of manifold 112. Preferably, channel 122 extends down angled annular inner surfaces 121a, 121b and down the pair of angled surfaces 115a of distal end portion 115 of manifold 112.

Third conduit 106 extends through manifold 112 and includes a distal end which is in fluid communication with channel 122. In this manner, as will be described in greater detail below, fluid transmitted from the third source "S3" of fluid, through third conduit 106, is dispensable or ejectable from channel 122 disposed between the inner surface 121a of cap 120 and the outer surface 115a of manifold 112. Nozzle 110 is disposed in connection member 32 so that the ejection ports 114 and 116, as well as proximal end of cap 120 are disposed in window 34a, 34b.

In use, as will be described in greater detail below, when a first fluid is dispensed from the plurality of proximal ejection ports 114 and a second fluid is dispensed from the plurality of distal ejection ports 116, the first and second fluids are mixed together by the third fluid dispensed from channel 122 which re-directs the path of dispersion of the second fluid into and across the path of dispersion of the first fluid. In other embodiments, the channel 122 may be eliminated and the surfaces of the dispersion system direct the fluid or fluids so as to mix them, or a member is movably mounted on distal end of the dispersion system, for mixing fluids.

The first source "S1" delivers a first fluid "W1" (e.g., a first part of a multi-part wound treatment material "W") through first conduit 102 to proximal ejection ports 114. The second source "S2" delivers a second fluid "W2" (e.g., a second part "W2" of the multi-part wound treatment material "W") through second conduit 104 to distal ejection ports 116. The third source "S3" delivers a third fluid, which may comprise gas "F" (e.g., air, $CO_2$, etc.) through third conduit 106 to channel 122. As will be described in greater detail below, the third fluid "F" functions to mix the first part "W1" with the second part "W2" of the wound treatment material "W" and to also direct the wound treatment material "W" toward the target tissue. In certain preferred embodiments, one or more of the fluid sources comprise cartridges removably connected to the handle assembly and which house the fluid. The cartridge or cartridges may be disposed within the handle assembly.

The delivery of the wound treatment material "W1, W2 and W3" may be accomplished utilizing one or more plungers in the conduits 102, 104 and/or 106, gas pressure, balloons, or pressure members for squeezing the conduits 102, 104, 106 to dispense the wound treatment material. The handle assembly includes a button, trigger or lever for actuating the delivery of the wound treatment material.

It is contemplated that the wound treatment material "W" is any material for joining, healing, sealing or otherwise treating tissue. In a preferred embodiment, the wound treatment material is a bio-compatible sealant, including, and not limited, to sealants which cure upon tissue contact, sealants which cure upon exposure to ultraviolet (UV) light, sealants which are multiple part systems, such as two-part systems, which are kept isolated from one another and are combined or any combinations thereof. Any known suitable adhesive may be used. In one embodiment, it is contemplated that such sealants and/or adhesives are curable. For example, sealants may have a cure time of from about 10 to 15 seconds may be used. In preferred embodiments, the sealant and/or adhesive is a bioabsorbable and/or bio-resorbable material. In another embodiment, it is contemplated that a sealant and/or adhesive having a cure time of about 30 seconds may be used. It is further envisioned that wound treatment material "W" may be a pre-cured adhesive or sealant. The pre-cured adhesive or sealant may react with the moisture and/or heat of the body tissue to thereby activate the sealing and/or adhesive properties of the sealant or adhesive.

In certain preferred embodiments, the wound treatment material comprises a sealant. Such a sealant is desirably a PEG-based material. Examples of classes of materials useful as the sealant and/or adhesive include acrylate or methacrylate functional hydrogels in the presence of a biocompatible photoinitiator, alkyl-cyanoacrylates, isocyanate functional macromers with or without amine functional macromers, succinimidyl ester functional macromers with amine or sulfhydryl functional macromers, epoxy functional macromers with amine functional macromers, mixtures of proteins or polypeptides in the presence of aldehyde crosslinkers, Genipin, or water-soluble carbodiimides, anionic polysaccharides in the presence of polyvalent cations, etc.

Some specific materials which may be utilized include isocyanate terminated hydrophilic urethane prepolymers derived from organic polyisocyanates and oxyethylene-based diols or polyols, including those disclosed in U.S. Pat. Nos. 6,702,731 and 6,296,607 and U.S. Published Patent Application No. 2004/0068078; alpha-cyanoacrylate based adhesives including those disclosed in U.S. Pat. No. 6,565,840; alkyl ester based cyanoacrylate adhesives including those disclosed in U.S. Pat. No. 6,620,846; adhesives based on biocompatible cross-linked polymers formed from water soluble precursors having electrophilic and nucleophilic groups capable of reacting and cross-linking in situ, including those disclosed in U.S. Pat. No. 6,566,406; two part adhesive systems including those based upon polyalkylene oxide backbones substituted with one or more isocyanate groups in combination with bioabsorbable diamine compounds, or polyalkylene oxide backbones substituted with one or more amine groups in combination with bioabsorbable diisoycanate compounds as disclosed in U.S. Published Patent Application No. 2003/0032734, the contents of which are incorporated by reference herein; and isocyanate terminated hydrophilic urethane prepolymers derived from aromatic diisocyanates and polyols as disclosed in U.S. Published Patent Application No. 2004/0115229, the contents of which are incorporated by reference herein.

It is envisioned and within the scope of the present disclosure that wound treatment material "W" may include one or a combination of adhesives, hemostats, sealants, or any other tissue or wound-treating material. Surgical biocompatible wound treatment materials "W", which may be used in accordance with the present disclosure, include adhesives whose function is to attach or hold organs, tissues or structures, sealants to prevent fluid leakage, and hemostats to halt or prevent bleeding. Examples of adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Denim Bond™ by Tyco Healthcare Group, LP and Ethicon Endosurgery, Inc., respectively. Examples of sealants, which can be employed, include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc. Examples of hemostat materials, which can be employed, include fibrin-based, collagen-based, oxidized regenerated cellulose-based and gelatin-based topical hemostats. Examples of commercially available hemostat materials are fibrinogen-thrombin combination materials sold under the trade designations CoStasis™ by Tyco Healthcare Group, LP, and Tisseel™ sold by Baxter International, Inc. Hemostats herein include astringents, e.g., aluminum sulfate, and coagulants.

The medicament may include one or more medically and/or surgically useful substances such as drugs, enzymes, growth factors, peptides, proteins, dyes, diagnostic agents or hemostasis agents, monoclonal antibodies, or any other pharmaceutical used in the prevention of stenosis.

Wound treatment material "W" may include visco-elastic film forming materials, cross-linking reactive agents, and energy curable adhesives. It is envisioned that wound treatment material "W", and in particular, adhesive may be cured with the application of water and/or glycerin thereto. In this manner, the water and/or glycerin cure the adhesive and hydrate the wound.

It is envisioned that wound treatment material "W" may be a relatively low viscosity fluid or liquid such that the wound treatment material "W" may freely flow through first and second conduits 102, 104 and out through proximal ejection ports 114 and distal ejection ports 116 of manifold 112, respectively. It is further envisioned that wound treatment material "W" may include a fine powder of particulate material.

It is further contemplated that wound treatment material "W" may include, for example, compositions and/or compounds which accelerate or beneficially modify the healing process when particles of the composition and/or compound are applied to or exposed to a surgical repair site. For example, the wound treatment material "W" may be a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, wound treatment material "W" may include one or several growth promoting factors, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

Figure 10:
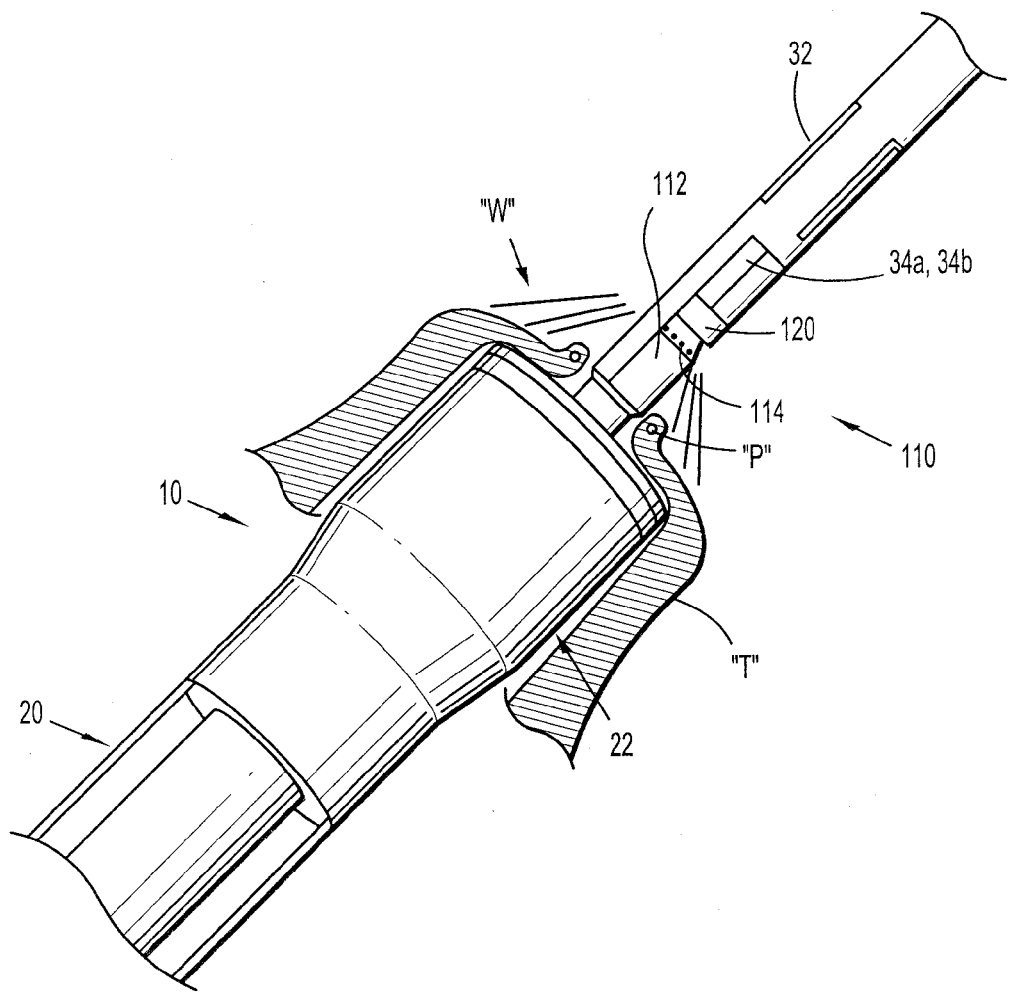
FIG. 10 is a schematic perspective view of the distal end of the surgical stapling apparatus of FIGS. 1-9 illustrating the placement thereof in a target surgical site.

With reference to FIGS. 1-10, and particularly FIG. 10, an exemplary method of using and operating surgical stapling apparatus 10 is shown and described. In operation, anvil assembly 26 is introduced into the operative site and a first organ or tissue to be joined or anastomosed is sutured around anvil assembly 26 by a purse string suture. Next, as seen in FIG. 10, the distal end of surgical stapling apparatus 10 is introduced into the operative site and sutured to a second organ or tissue "T" by a purse string suture "P" which is to be joined or anastomosed to the first organ or tissue. Desirably, the second organ or tissue "T" is sutured around inner rod member 40 such that the purse string suture "P" is located proximally of nozzle 100.

With anvil assembly 26 and the distal end of surgical stapling apparatus 10 sutured into position stem 26b of anvil assembly 26 is coupled to connection member 32 of surgical stapling apparatus 10. Either prior to or after the coupling of stem 26b of anvil assembly 26 to connection member 32 of surgical stapling apparatus 10, wound treatment material dispensing system 100 is activated to dispense wound treatment material "W" onto the second organ or tissue "T", by manipulating a button, lever, or trigger on handle assembly 12.

In particular, as seen in FIGS. 9 and 10, first part "W1" of a multi-part wound treatment material "W" is conducted from the first source of fluid "S4", through first conduit 102, for dispersion and/or ejection from the plurality of proximal ejection ports 114 of manifold 112. A second part "W2" of the multi-part wound treatment material "W" is conducted, from the second source of fluid "S2", through second conduit 104, for dispersion and/or ejection from the plurality of distal ejection ports 116 of manifold 112. As seen in FIG. 9, third fluid "F" (e.g., air, $CO_2$, etc.) is conducted from the third source of fluid "S3", through third conduit 106, for dispensing and/or ejection from channel 122. Third fluid "F" functions to re-direct the path of dispersion of second part "W2" of wound treatment material "W" into and across the path of dispersion of first part "W1" of wound treatment material "W". Third fluid "F" also functions to mix the second part "W2" of wound treatment material "W" with the first part "W1" of wound treatment material "W". The third fluid "F" directs the mixed wound treatment materials "W1, W2" in a substantially proximal direction against the second organ or tissue "T". Desirably, the fluids "W1, W2" and "F" are dispensed through their respective conduits about simultaneously.

Desirably, first part "W1" of wound treatment material "W" is a first-part of a multi-part sealant and second part "W2" of wound treatment material "W" is a second-part of the multi-part sealant. Activation of the sealant is achieved upon mixing of the first and second parts together at the desired and/or appropriate time during the surgical procedure. Premature mixing of the first and second parts of the two-part sealant may result in premature curing, clogging or gumming up of components of surgical stapling apparatus 10 and the like. Accordingly, wound treatment material dispersion system 100 maintains the first and second parts of the two-part sealant separate from one another until the first and second parts are ejected from nozzle 110.

With wound treatment material "W" dispensed onto the second organ or tissue "T" and with stem 26b of anvil assembly 26 coupled to connection member 32 of surgical stapling apparatus 10, anvil assembly 26 is approximated toward staple pusher member 22 by rotating knob member 18. Rotation of knob member 18 in a first direction causes approximation assembly 30 to move in a proximal direction thereby drawing anvil member 26a of anvil assembly 26 into position adjacent staple pusher member 22 and to locate the ends of the tissue between these two members. Knob member 18 is rotated until the desired and/or necessary distance between anvil member 26a and staple pusher member 22 has been achieved. Desirably, the two opposed tissues are brought into contact with one another.

Once the proper distance is set between anvil member 26a of anvil assembly 26 and staple pusher member 22, surgical stapling apparatus 10 is fired by squeezing, e.g., pivoting, actuating handle member 16 toward fixed handle member 14 (see FIGS. 1 and 2). In so doing, stem 16a of actuating handle member 16 presses against nub 56 of bushing 52 of drive assembly 50 and causes drive assembly 50 to move in a distal direction. As discussed above, movement of drive assembly 50 in a distal direction results in compression of biasing member 60 and movement of drive arms 58 in a distal direction to actuate staple pusher member 22. As a result, the staples are driven out of or ejected from body portion 20, through the tissue or organ, and against the anvil member 26a to complete the circular anastomosis of the tubular organ.

Following firing of surgical stapling apparatus 10, actuating handle member 16 may be released. Release of actuating handle member 16 allows for biasing member 60 to expand, thereby moving drive assembly 50 and, in particular bushing 52, in a proximal direction. As bushing 52 moves in a proximal direction, nub 56 thereof presses against stem 16a of actuating handle member 16 causing actuating handle member 16 to return to the un-squeezed or un-approximated condition.

Desirably, application of wound treatment material "W" to the anastomosis site may help to reduce the incidence of anastomotic leakage by sealing the surfaces of the organs and/or tissues of the anastomosis against one another. It is further envisioned that application of wound treatment material "W" to the anastomosis site may help to adhere the anastomosed ends of the organs and/or tissues to one another.

Desirably, in accordance with an embodiment of the present disclosure, surgical stapling apparatus 10 may include an annular knife blade (not shown) operatively associated therewith. Desirably, the annular knife blade is disposed radially inwardly of the annular array of staple pockets 24, but outwardly of inner rod member 40. A distal end of the annular knife blade includes a cutting edge for severing the tissue located radially inwardly of the annular knife blade from the tissue located radially outwardly of the annular knife blade. Desirably, in operation, as surgical stapling apparatus 10 is fired to drive the staples through the layers of tissue, the annular knife blade is simultaneously advanced to sever the portion of tissue disposed radially inwardly of the annular knife from the remaining tissue.

In further embodiments, the manifold 112 includes one array of ports in communication with a source of fluid "S1". The channel 122 and angled surfaces 121a and 121b are utilized to dispense a second fluid from source "S2". Alternatively, a one part material is dispensed through the array of ports and the channel 122 and angled surfaces 121a and 121b are utilized to dispense a fluid "F" (such as $CO_2$ gas or air) for directing the fluid dispensed through the array of ports. In further embodiments, the manifold 112 does not include an array of ports and the channel 122 and angled surfaces 121a and 121b are used to dispense a one part material.

In further embodiments, the wound treatment material dispersion system 100 is incorporated into a device with a tubular body portion and anvil assembly, but without the deployment of staples. The wound treatment material is relied upon to join the generally tubular organ portions.

Figure 12:
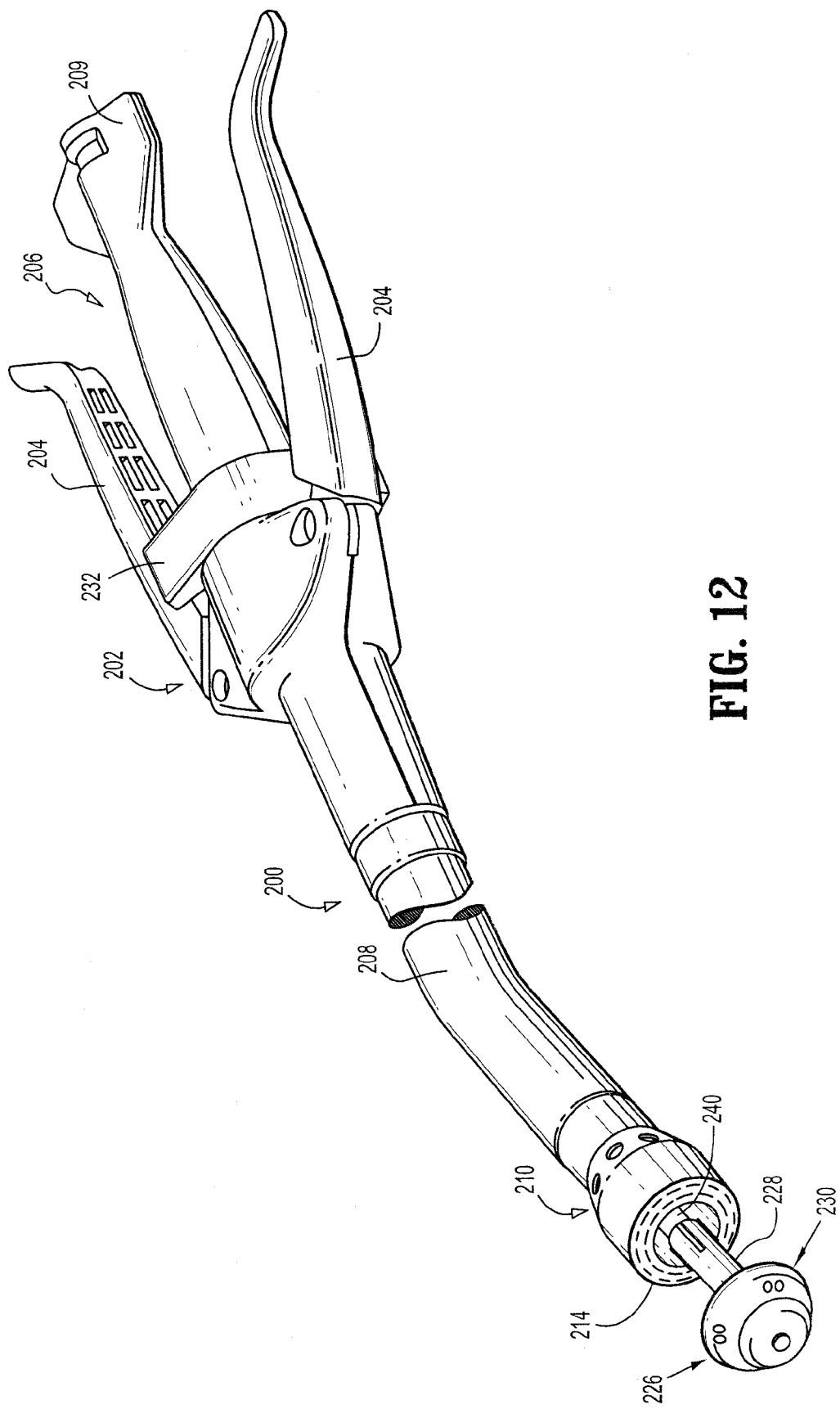
FIG. 12 illustrates a perspective view of a surgical stapling apparatus according to another embodiment of the present disclosure.

Referring now in specific detail to FIG. 12 a surgical stapling apparatus employing structure for applying a dispersible wound treatment material according to an alternate embodiment of the present disclosure is generally designated as 200. Apparatus 200 includes a handle assembly 202 having at least one pivotable actuating handle member 204, and further includes advancing means 206 a rotatable grip member 209.

Extending from handle assembly 202, there is provided a tubular body portion 208 which may be constructed so as to have a curved shape along at least a portion of its length. Tubular body portion 208 may also be straight, or in other embodiments, tubular body portion 208 may be flexible to bend to any configuration. Body portion 208 terminates in a staple pusher member 210. Staple pusher member 210 includes an annular array of staples 214. Positioned opposite staple pusher member 210 there is provided an anvil assembly 226 including an anvil member 230 which is connected to apparatus 200 by stem 228 at connection means 240. Anvil assembly 226 and staple pusher member 210 are disclosed in commonly assigned U.S. Pat. No. 5,119,983, issued Jun. 9, 1992, which is incorporated herein by reference.

While apparatus 200 is shown and described as utilizing a staple pusher member having an annular array of staples positioned on the tubular body portion, and having the anvil member positioned opposite the staple pusher member for movement towards and away from the staple pusher member, it is of course contemplated that the anvil member may be positioned on the tubular body portion and the staple pusher member and array of staples be positioned opposite the anvil member for movement towards and away from the anvil member. Such a construction is to be considered within the scope of the present disclosure.

In operation, apparatus 200 is positioned within a tubular organ in the body of the patient and the ends of the organ to be joined are positioned in the gap between staple pusher member 210 and anvil assembly 226 so that anvil assembly 226 is fully extended. As is conventional, the ends of the organ may be secured over anvil assembly 226 and staple pusher member 210 by a purse string suture prior to approximation of anvil assembly 226 in relation to staple pusher member 210. With anvil assembly 226 and staple pusher member 210 purse string sutured, stem 228 of anvil assembly 226 is coupled to connection means 240 disposed within staple pusher member 210.

In order to approximate anvil assembly 226 towards staple pusher member 210, grip member 209 is rotated to displace an inner rod member (not shown) in a proximal direction. This draws anvil assembly 226 into position adjacent staple pusher member 210 and locates the ends of the tissue between these two members.

Once the proper distance is set between anvil assembly 226 and staple pusher member 210 interlock means 232 may be released and actuating handles 204 may be pivoted to drive the staples through the tissue and against anvil member 230 to complete the circular anastomosis of the tubular organ. Reference may be made to U.S. Pat. No. 5,119,983, previously incorporated herein by reference for a more detailed description and discussion of the structure and operation of surgical stapling apparatus 200.

Figure 13:
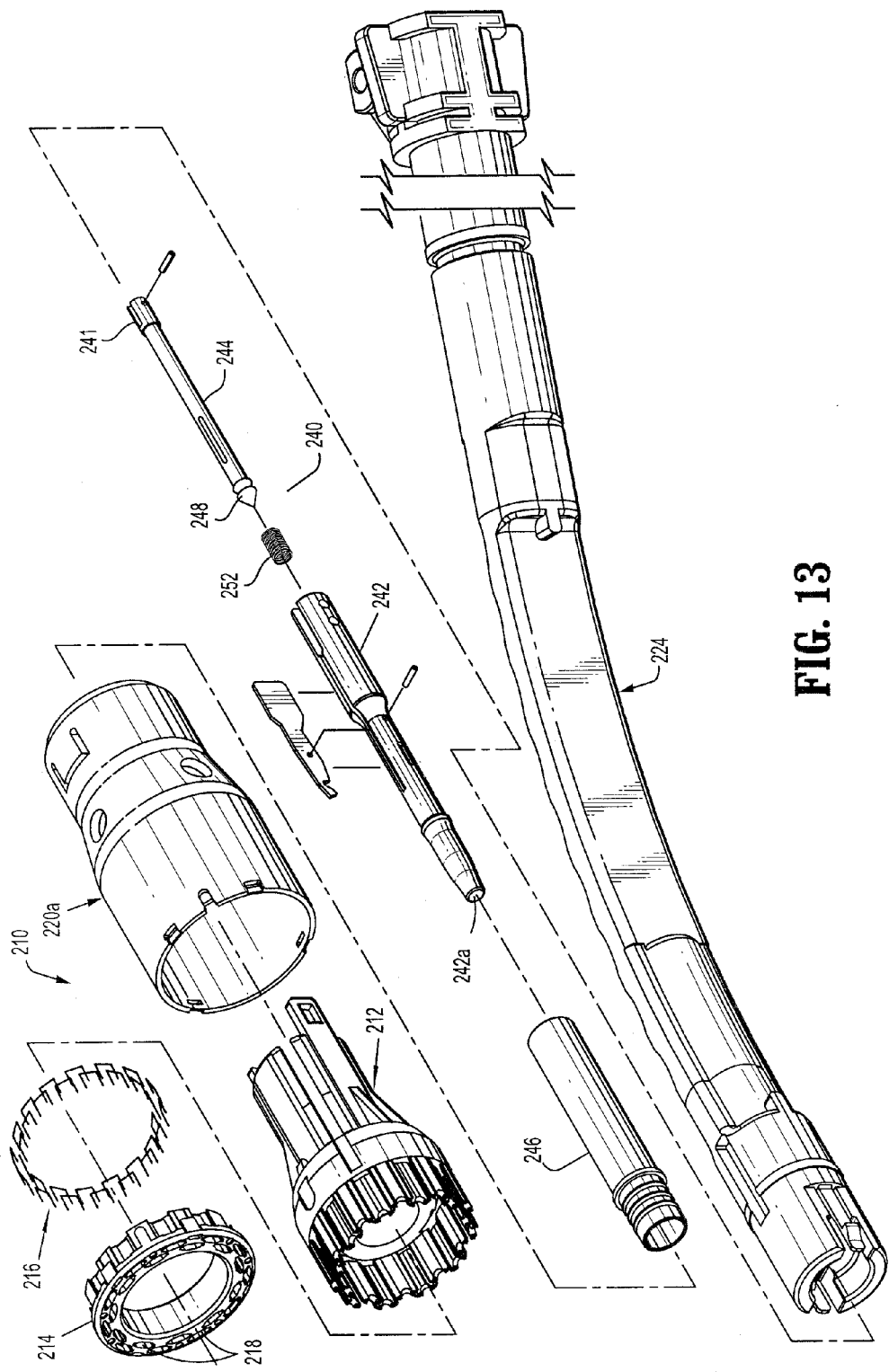
FIG. 13 is an exploded perspective view of the distal end of the surgical stapling apparatus of FIG. 12.
Figure 14:
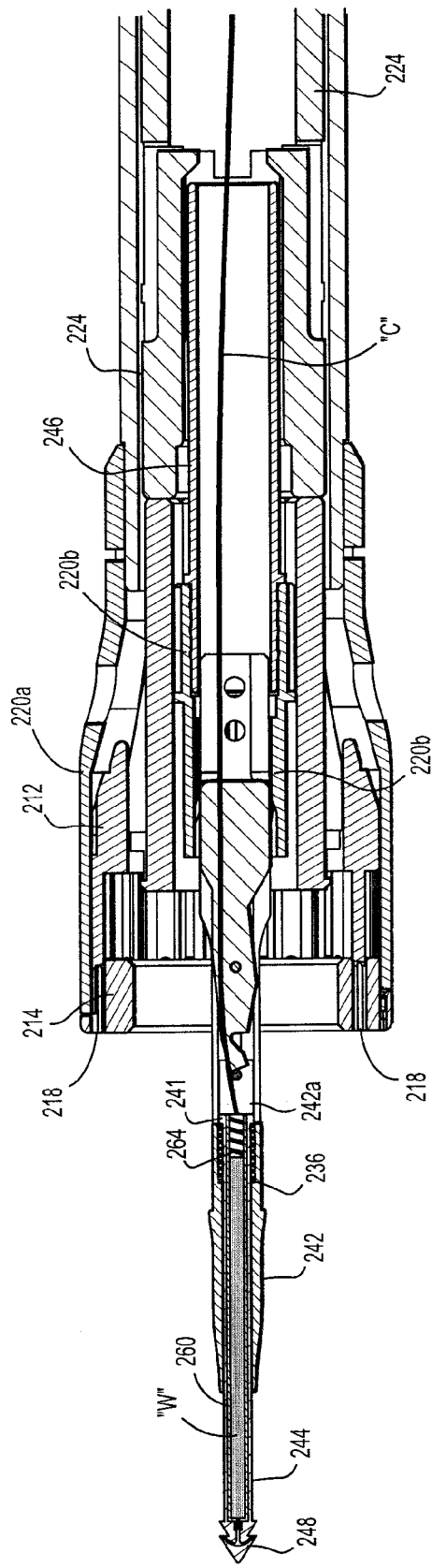
FIG. 14 is a longitudinal cross-sectional view of the distal end of the surgical stapling apparatus of FIG. 13.

With reference to FIGS. 13 and 14, staple pusher member 210 of surgical stapling apparatus 200, is shown and described. Although not shown or discussed herein, connection means 240 is connected to an approximation mechanism and pusher 224 is connected to the firing mechanism of surgical stapling apparatus, such as, for example, pivotable actuating handle members 204 (see FIG. 1).

Staple pusher member 210 includes a housing 220, a pusher 212, an annular knife blade (not shown), a staple guide 214, and a plurality of staple 216. As seen in FIG. 14, housing 220 includes an outer housing portion 220a and an inner housing portion 220b. Staple guide 214 is supported in the distal end of outer housing portion 220a and includes an annular array of staple receiving pockets 218 for housing staples 216. Pusher 212 is slidably supported in housing 220 between outer housing portion 220a and inner housing portion 220b and is slidable between retracted and advanced positions.

An elongated hollow bushing 246 is fixedly retained in inner housing portion 220b of housing 220. Bushing 246 defines a lumen through which connection means 240 reciprocates during approximation and separation of staple anvil assembly 226 and staple pusher member 224.

Connection means 240 includes a two-part trocar assembly having a body portion 242 defining a longitudinal throughbore 242a and a trocar 244 slidably received within longitudinal throughbore 242a of body portion 242. Desirably, longitudinal throughbore 242a includes a stepped portion or shoulder 236 (see FIG. 14).

Trocar 244 includes a tip 248 at one end thereof and an annular flange 241 at the other end thereof. Tip 248 of trocar 244 extends from a distal end of body portion 242 of the trocar assembly and is movable from an advanced position to a retracted position. Desirably, tip 248 is sharpened thereby enabling tip 248 to penetrate tissue and the like. A biasing member, preferably a coil spring 252, is positioned between annular flange 241 of trocar 244 and shoulder 236 and urges trocar 244 to its retracted position.

Turning now to FIGS. 15-17, trocar 244 forms a part of a wound treatment material dispersion system, according to an embodiment of the present disclosure. Trocar 244 is preferably hollow and is sized to receive an ampoule 260 or the like therein. Ampoule 260 includes a body portion 262 having a nub 263 extending axially therefrom, and defining a lumen 262a extending through each of body portion 262 and nub 263. Nub 263 has a smaller cross-sectional dimension than body portion 262 and defines a shoulder 263a. Ampoule 260 further includes a plunger 264 slidably disposed within lumen 262a. Plunger 264 forms a fluid tight seal with the inner surface of body portion 262. Desirably, wound treatment material "W" is retained within lumen 262a of ampoule 260.

As seen in FIGS. 15-17, trocar 244 defines a cavity 229 for selectively receiving ampoule 260 therein. A distal end of cavity 229 defines a distal pocket 229a configured to receive nub 263 of ampoule 260 therein. Pocket 229a is dimensioned such that a shoulder 263a of ampoule 260 contacts or engages a corresponding shoulder 229b formed in cavity 229.

Trocar 244 further includes a channel 245a extending from distal pocket 229a and which branches off into a series of ports 245b formed radially around tip 248. Preferably, ports 245b are angled in a proximal direction. Preferably, trocar 244 includes a two-tiered tip 248 having a distal-most conical tip 248a and a proximal-most conical tip 248b. Desirably, ports 245b are formed between distal-most conical tip 248a and proximal-most conical tip 248b such that ports 245b are formed in a proximal surface of distal-most conical tip 248a. In this manner, when ampoule 260 is placed within cavity 229 of trocar 244, lumen 262a of ampoule 260 is in fluid communication with ports 245b. As seen in FIG. 15, ports 245b act like a manifold to divide the dispersion of wound treatment material "W" to different radial segments around trocar 244.

In operation, as seen in FIG. 17 and as will be described in greater detail below, upon distal advancement of plunger 264 through lumen 262a of ampoule 260 (in the direction of arrow "A"), wound treatment material "W" is forced through nub 263, into distal pocket 229a, and out through ports 245b. It is envisioned that a piston, rod or some other device or method (e.g., pneumatic) may be used to advance plunger 264 distally through lumen 262a.

Figure 19:
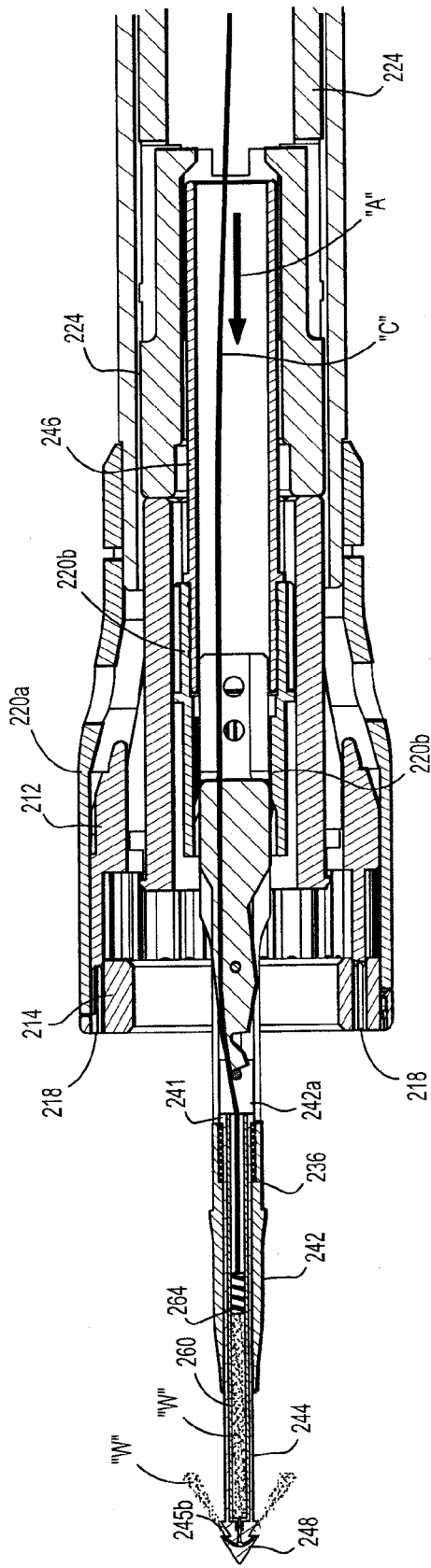
FIG. 19 is a longitudinal cross-sectional view of the distal end of the surgical stapling apparatus of FIG. 14, illustrating the displacement of the drive cable to dispense the wound treatment material from the wound treatment material dispensing system.

Preferably, as seen in FIGS. 14 and 19, surgical stapling apparatus 200 includes a piston or drive cable "C" extending therethrough. Drive cable "C" includes a distal end which contacts and/or engages or is operatively engaged with plunger 264 of ampoule 260. Desirably, cable "C" is sufficiently flexible to bend and flex through surgical stapling apparatus 200 and sufficiently rigid to transmit forces along the length thereof. In this manner, as will be discussed in greater detail below, with a distal end of drive cable "C" in operative engagement with plunger 264, as drive cable "C" is distally advance through surgical stapling apparatus 200, drive cable "C" advances plunger 264 through lumen 262a of ampoule 260 to thereby force wound treatment material "W" therefrom.

Figure 18:
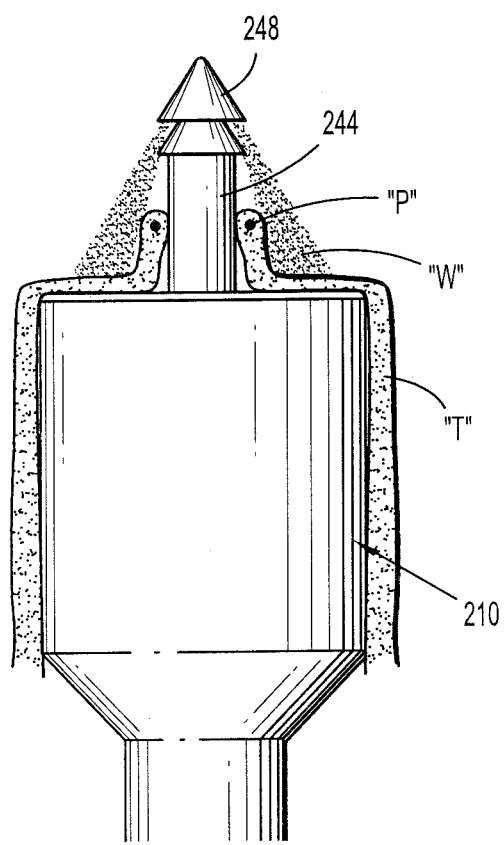
FIG. 18 is a schematic illustration of a distal end of the surgical stapling apparatus of FIG. 12, including the wound treatment material dispensing system of FIGS. 15-17 operatively associated therewith, illustrating the dispersing of wound treatment material therefrom according to a method of the present disclosure.

Turning now to FIGS. 18 and 19, use of the wound treatment material dispersion system, including trocar 244, of FIGS. 13-17, in connection with surgical stapling apparatus 200, is shown and described. In operation, anvil assembly 226 is introduced into the operative site and sutured to a first organ or tissue to be joined or anastomosed by a purse string suture. Next, with ampoule 260 positioned within trocar 244, the distal end of surgical stapling apparatus 200 is introduced into the operative site and sutured to a second organ or tissue by a purse sting suture "P" which is to be joined or anastomosed to the first organ or tissue. Desirably, the second organ or tissue is sutured to trocar 244 and/or connection means 240 such that purse string "P" is located proximal of ports 245b.

With anvil assembly 226 and staple pusher member 210 sutured in place, as seen in FIG. 19, a piston or drive cable "C" of connection means 240 is advanced in a distal direction (e.g., in the direction of arrow "A") to drive plunger 264 through lumen 262a of ampoule 260 and force wound treatment material "W" contained therein out through channel 245a of trocar 244 and, in turn, out through ports 245b. Since ports 245b are angled in a proximal direction, wound treatment material "W" is dispensed onto the second organ or tissue to be anastomosed.

With the second organ or tissue at least partially coated with wound treatment material "W", stem 228 of anvil assembly 226 is coupled to connection means 240 of staple pusher member 210. Anvil assembly 226 is then approximated towards staple pusher member 210 by rotating grip member 218 to thereby draw anvil assembly 226 into position adjacent staple pusher member 210 and locates the ends of the tissue between these two members.

Once the proper distance is set between anvil member 230 and staple pusher member 210, actuating handles 204 may be pivoted to drive the staples through the tissue or organ and against anvil member 230 to complete the circular anastomosis of the tubular organ. Reference may be made to U.S. Pat. No. 5,119,983, the entire contents of which are incorporated herein by reference, for a more detailed description and discussion of the operation of surgical stapling apparatus 200.

Figure 20:
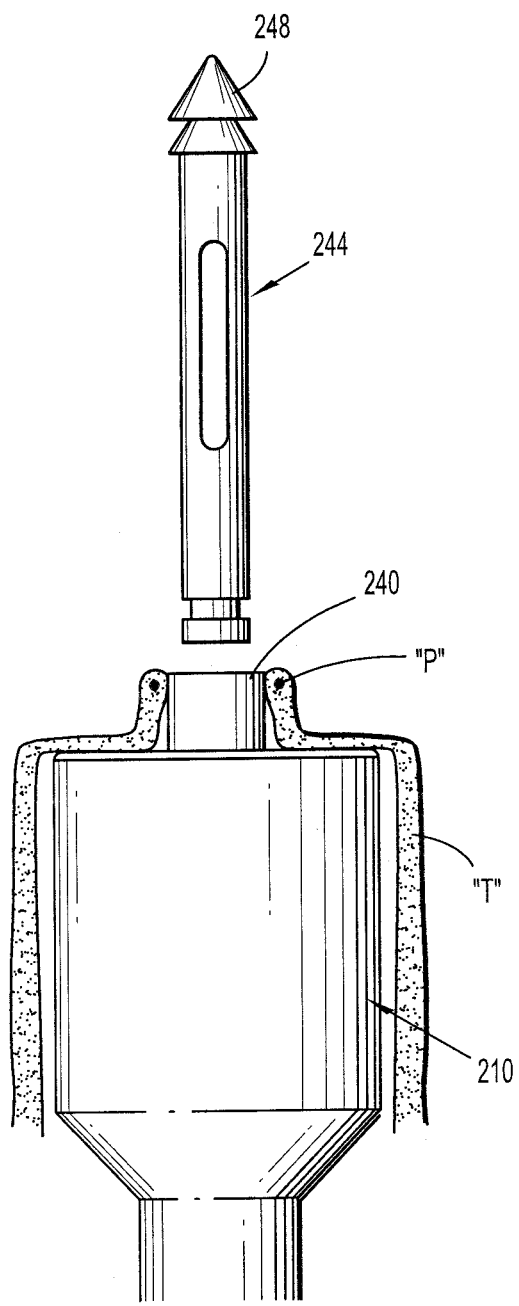
FIG. 20 is a schematic illustration of a distal end of the surgical stapling apparatus of FIG. 12, illustrating the removal of the wound treatment material dispensing system of FIGS. 15-17 from the distal end of the surgical stapling apparatus of FIG. 12.

According to another method of use, as seen in FIG. 20, following dispensing of wound treatment material "W" onto the second organ or tissue, trocar 244 is removed from connection means 240 and stem 228 of anvil assembly 226 is operatively connected or otherwise docked thereto. With anvil assembly 226 operatively connected to connection means 240, anvil assembly 226 is approximated toward staple pusher member 210 and surgical stapling apparatus 200 is fired as described above.

Desirably, application of wound treatment material "W" to the anastomosis site may help to reduce the incidence of anastomosis leakage by sealing the surfaces of the organs and/or tissues of the anastomosis against one another. It is further envisioned that application of wound treatment material "W" to the anastomosis site may help to adhere the anastomosed ends of the organs and/or tissues to one another.

It is envisioned that wound treatment material "W" may be a substantially non-viscous fluid or liquid such that the wound treatment material "W" may freely flow from ports 245b of trocar 244.

It is provided that a number of different wound treatment materials "W" can be dispensed by trocar 244 of the wound treatment material applicator assembly. The wound treatment material dispensed by wound treatment material applicator assembly can, for example, include any and/or all of the wound treatment materials disclosed above.

Figure 21:
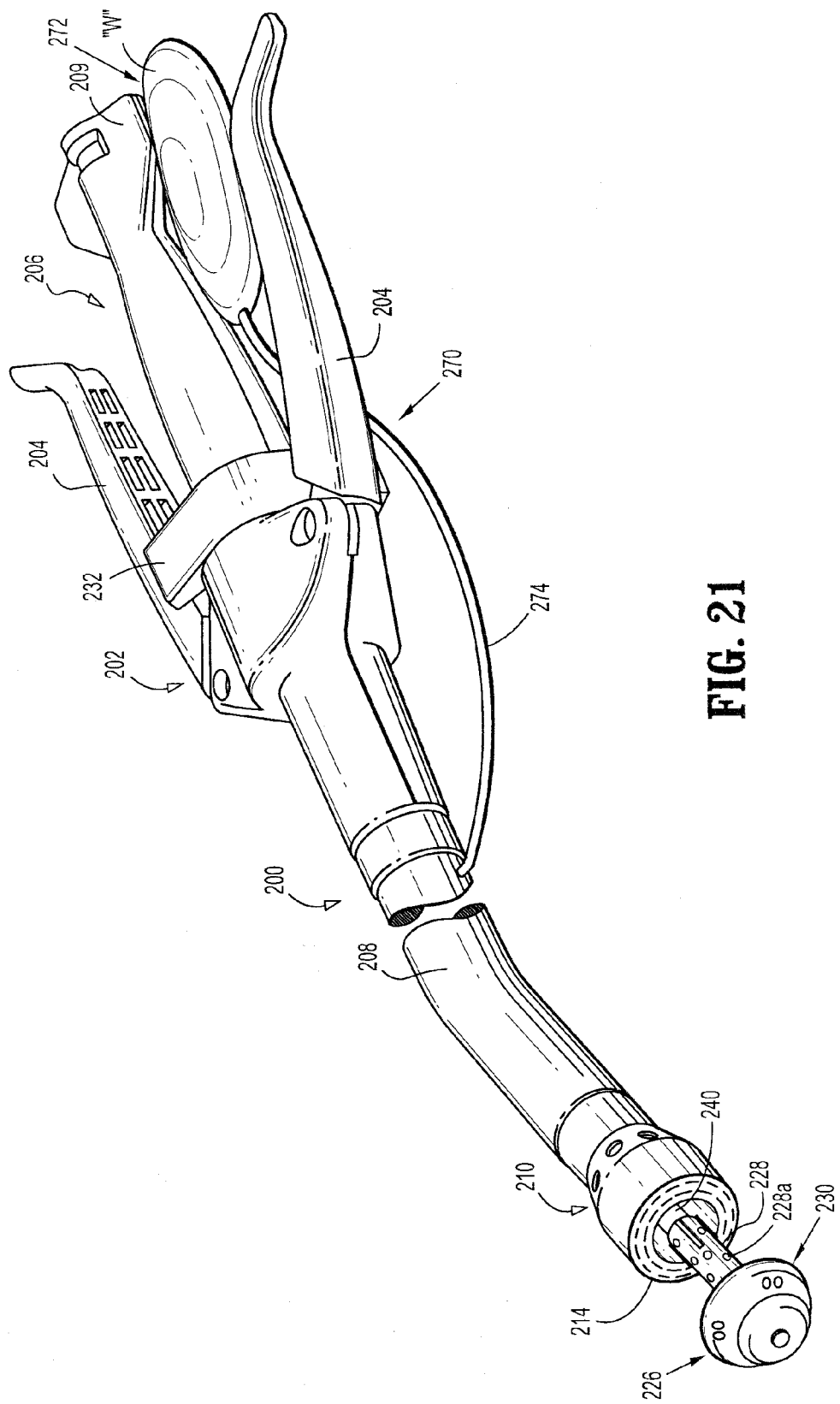
FIG. 21 illustrates a perspective view of a surgical stapling apparatus according to an alternate embodiment of the present disclosure.
Figure 22:
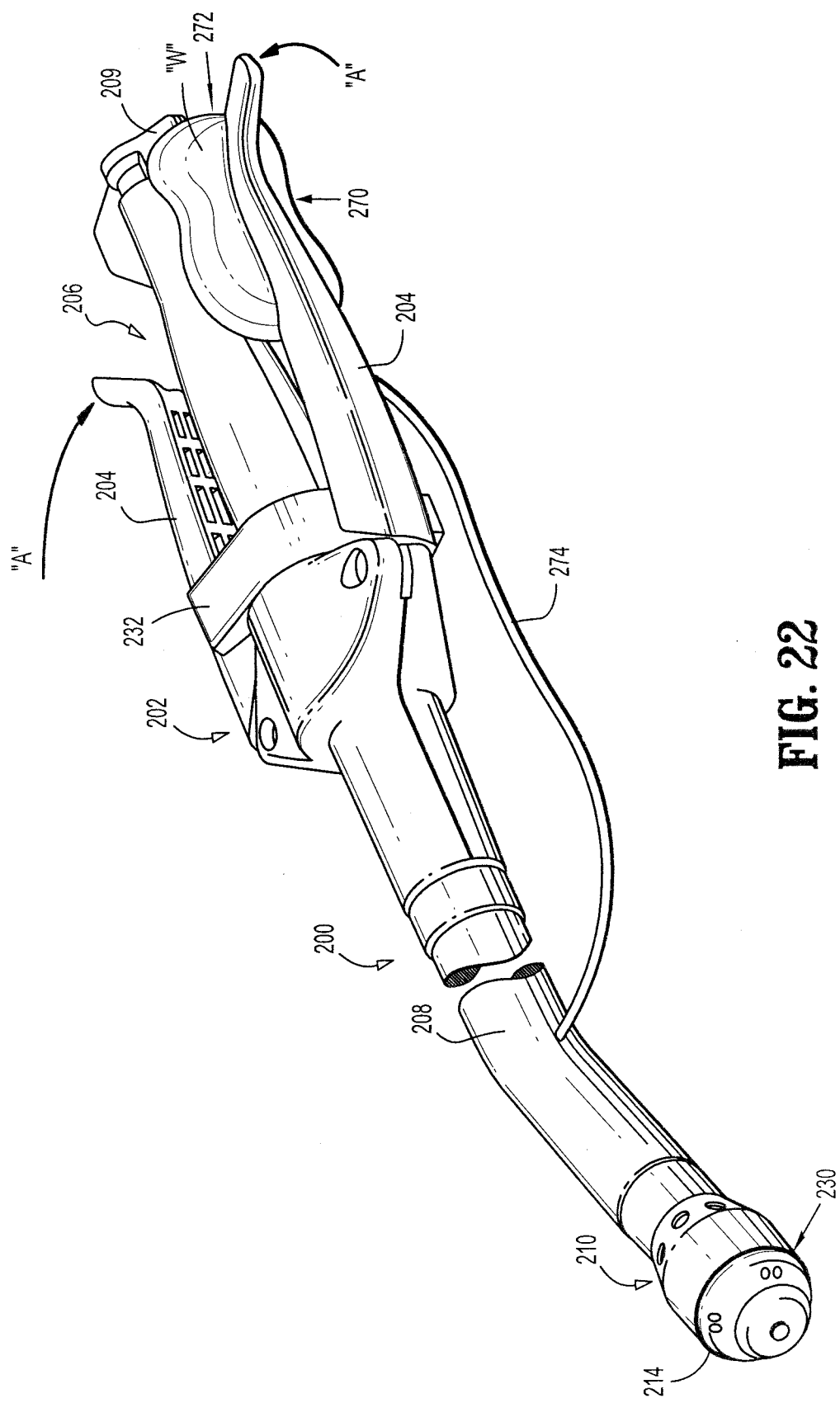
FIG. 22 is a perspective view of the surgical stapling apparatus of FIG. 21 illustrating an exemplary method of dispensing the wound treatment material from the stem of the anvil assembly.
Figure 23:
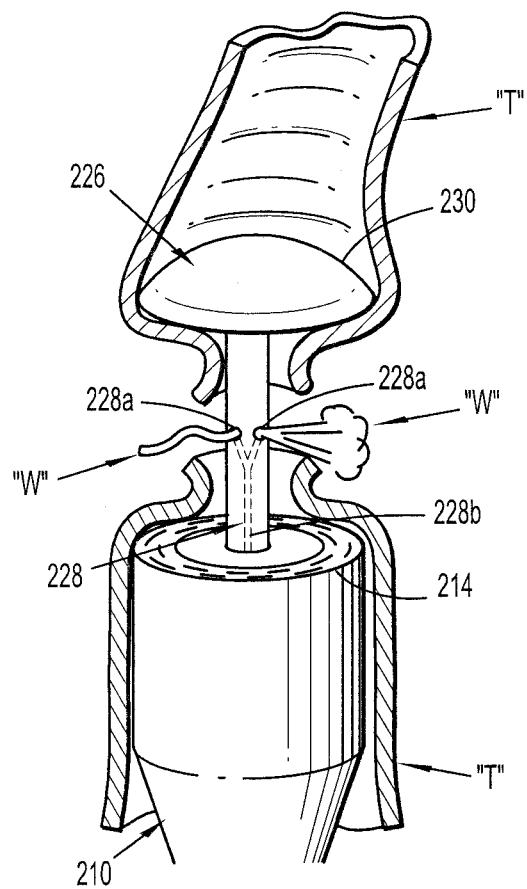
FIG. 23 is a schematic illustration of the surgical stapling apparatus of FIGS. 21 and 22 depicting the dispensing of wound treatment material from a stem of an anvil assembly.

According to an alternate embodiment of the present disclosure, as seen in FIGS. 21 and 22, surgical stapling apparatus 200 further includes a wound treatment material applicator assembly 270 for applying wound treatment material "W" to a target tissue "T" (see FIG. 23). Wound treatment material "W" may include and is not limited to at least one biological and/or synthetic biocompatible sealant, hemostat, adhesive, and combinations thereof. Wound treatment material "W" may be applied to target tissue "T" either before, during or after firing of the annular array of staples 216 (see FIG. 13). The application of wound treatment material "W" to a knife cut line and/or staple line can provide short, i.e., temporary, and long-term, i.e., permanent, hemostasis and sealing, and reduce or prevent bleeding along the knife cut line and/or staple line, while the stapling features provide short and long-term tissue strength and hemostasis.

If used without staples 216, surgical stapling apparatus 200 provides an anastomosis capable of greater elasticity resulting in lower possibility of stricture at the site. If used with staples, surgical stapling apparatus 200 provides greater initial strength, with lower possibility of leakage of bowel contents. Additionally, since knife cut line and staple line bleeding is reduced or prevented, the surgical stapling apparatus 200 of the present invention makes it possible to expand the applicable range of specific staple sizes to include thinner or thicker staples.

As seen in FIGS. 21 and 22, wound treatment material applicator assembly 270 includes at least one reservoir 272 fluidly connectable or connected to a passage 228b (see FIG. 23) formed in connection means 240. Desirably, reservoir 272 is compressible and is affixed or mounted to a pivotable actuating handle member 204 or disposed between actuating handle member 204 and grip member 209. Reservoir 272 may be in fluid communication with stem 228 of anvil assembly 226 via a conduit 274 fluidly connecting reservoir 272 to passage 228b of stem 228.

In use, wound treatment material applicator assembly 270 supplies wound treatment material "W", or a component thereof, to a target surgical site upon compression of reservoir 272 between handle member 204 and grip member 209. In one exemplary embodiment, as seen in FIGS. 21 and 22, by moving pivotable actuating handle members 204 towards grip member 209, as indicated by arrow "A", reservoir 272 is squeezed or compressed therebetween.

Compression of reservoir 272 causes wound treatment material "W" contained therein to be urged through conduit 274 and dispensed via holes 228a of anvil stem 228. As seen in FIG. 23, wound treatment material "W" may be dispensed before or during the staple firing procedure so that wound treatment material "W" is dispensed along the length of the staple line and/or along a circular knife cut line and along the surfaces of target tissues "T" which are to come into contact with one another. Other methods of initiating the dispensing of the wound treatment material "W" from anvil stem 228 are envisioned, such as, for example, dispensing of wound treatment material "W" upon actuation of the circular knife, movement of anvil assembly member 226 towards the fastener assembly, and the like.

During dispensing, wound treatment material "W" is ejected into or onto the space between the tissue surfaces clamped between movable anvil member 230 and staple pusher member 210. Ejection of wound treatment material "W" occurs by spraying, squirting, and/or foaming. During ejection of wound treatment Material "W" it is preferred that anvil stem 228 rotates so that wound treatment material "W" is spread radially over and along the clamped tissue surfaces.

While a single reservoir 272 for containing wound treatment material "W" is shown and described, it is envisioned and within the scope of the present disclosure for any number of reservoirs to be fluidly connected to passage 228b of stem 228. In such an embodiment, one or a first reservoir may store one component of wound treatment material "W" and another or a second reservoir may store a second component of wound treatment material "W". Preferably, the first and second reservoirs are identical and encase or store an equal or appropriate volumetric amount of their respective component of wound treatment material "W" to maintain a predetermined desired ratio of the first component of the wound treatment material "W" to the second component of the wound treatment material "W", which is typically a 1:1 ratio.

Preferably, the wound treatment material "W" formed by the two components is a fibrin glue or a fibrin sealant, which acts as a hemostatic agent and as a tissue adhesive. Fibrin sealant is formed by a rapid polymerization process, which occurs when a solution of proteomic clotting factors, such as fibrinogen, comes into contact with a solution of a proteomic catalyst, such as thrombin. This rapid polymerization typically commences within two seconds after the solutions initially contact one another, and it typically attains a soft set within ten seconds of contact. Because of the rapid polymerization upon intimate interaction of fibrinogen and thrombin, it is important and preferable to maintain these two blood proteins separate until applied at the application site. Accordingly, in an alternative embodiment the wound treatment material applicator assembly 270 supplies each blood protein separately from the other blood protein by using a separate conduit for each protein.

It is envisioned that reservoir 272 of applicator assembly 270 may contain any one or any combination of the wound treatment materials "W" disclosed above.

It is to be understood that the dispensing of wound treatment material "W" can be a fluid spray of any suitable volume, including a mist, applied temporarily, continuously, or continually. Particulate material, e.g. a fine powder is contemplated to be a fluid within the scope of this disclosure.

It is envisioned and within the scope of the present disclosure for the wound treatment material "W" to be dispensed, from either surgical stapling apparatus 100, 200, in an aerosol form. For example, with reference to FIG. 2, third source "S3" may be an aerosol can containing a propellant (e.g., compressed air, $CO_2$, etc.) therein which is used to atomize the wound treatment material "W" during dispensing of wound treatment material "W" to the target tissue.

In further embodiments, the conduit 274 is incorporated within tubular body portion 208 and/or the reservoir 272 is incorporated into the grip member 206. The conduit 274 shown in FIG. 22 may be connected to the tubular body portion 208 closer to the handle assembly 202, so that the conduit 274 does not interfere with the insertion of the device into a patient or a patient's organs.

It will be understood that various modifications may be made to the embodiments of the presently disclosed surgical stapling apparatus and the wound treatment material dispersion system described above. Therefore, the above description should not be construed as limiting, but merely as exemplifications of preferred embodiments. Those skilled in the art will envision other modifications within the scope and spirit of the present disclosure.

What is claimed is:

1. An apparatus for forming an anastomosis between adjacent sections of tissue, comprising:
   a body portion;
   an anvil assembly movably mounted at a distal end of the body portion for movement toward and away from the body portion;
   an approximation assembly extending between the body portion and the anvil assembly for moving the anvil assembly toward and away from the body portion;
   a dispersion assembly operatively associated with the approximation assembly, the dispersion assembly including at least one angled surface relative to the longitudinal axis of the body portion defining at least one channel interposed between the anvil assembly and the body portion and being configured to dispense a fluid therefrom, wherein the dispersion assembly includes a manifold having a plurality of ejection ports for dispensing:
   a first wound treatment material; and
   a second wound treatment material; and
at least one conduit for conducting the first and second wound treatment material to the dispersion assembly,
wherein a distal end portion of the manifold is tapered at an angle relative to the longitudinal axis of the body portion.

2. The apparatus according to claim 1, wherein the at least one conduit includes:
   a first conduit having a distal end in fluid communication with a plurality of first ejection ports formed in the manifold; and
   a second conduit having a distal end in fluid communication with a plurality of second ejection ports formed in the manifold.

3. The apparatus according to claim 2, the plurality of first ejection ports and the plurality of second ejection ports are disposed in the distal end portion of the manifold.

4. The apparatus according to claim 3, wherein the dispersion assembly further includes:
   a cap operatively connected to the distal end of the manifold in such a manner so as to define a channel between an outer surface of the distal end portion of the manifold and an inner surface of the cap.

5. The apparatus according to claim 2, further comprising:
   a third conduit having a distal end in fluid communication with a third ejection port.

6. The apparatus according to claim 5, wherein the first conduit is connectable to a first fluid source, the second conduit is connectable to a second fluid source, and the third conduit is connectable to a third fluid source.

7. The apparatus according to claim 6, wherein the first fluid source includes a first part of a multi-part wound treatment material, and wherein the second fluid source includes a second part of the multi-part wound treatment material.

8. The apparatus according to claim 7, wherein the multi-part wound treatment material is a sealant.

9. The apparatus according to claim 6, wherein the third source includes a fluid.

10. The apparatus according to claim 4, wherein the cap and the distal end portion of the manifold are shaped so that the channel directs the fluid in a substantially proximal direction.

11. The apparatus according to claim 7, wherein the fluid ejected from the channel causes the first and second parts of the multi-part wound treatment material to mix.

12. The apparatus according to claim 1, further comprising an actuation assembly having at least one handle connected to the body portion.

13. The apparatus according to claim 12, wherein the approximation assembly includes:
   a threaded rod member threadingly engaging the at least one handle; and
   a knob member operatively connected to a proximal end of the threaded rod member.

14. The apparatus according to claim 13, wherein the dispersion assembly is operatively associated with the distal end of the threaded rod member.

15. The apparatus according to claim 14, wherein the threaded rod member includes windows formed on opposite sides thereof, wherein the windows are in registration with the at least one ejection port.

16. The apparatus according to claim 15, wherein the distal end of the threaded rod member comprises a connection member defining the windows, wherein a distal end of the connection member is configured to selectively engage a stem of an anvil assembly.

17. An apparatus for forming an anastomosis between adjacent sections of tissue, the apparatus comprising:
   a body portion;
   an anvil assembly movably mounted at a distal end of the body portion for movement toward and away from the body portion;
   an approximation assembly extending between the body portion and the anvil assembly for moving the anvil assembly toward and away from the body portion;
   a dispersion assembly operatively associated with the approximation assembly, the dispersion assembly including:
      a manifold having a plurality of ejection ports for dispensing at least a first and second wound treatment material;
      a cap operatively connected a distal end of the manifold; and
      a channel defined by a surface of the manifold and an inner surface of the cap for dispensing a fluid therefrom.

18. The apparatus according to claim 17, wherein the channel is angled at approximately fifteen degrees relative to the central longitudinal axis of the manifold.

19. The apparatus according to claim 17, wherein the channel is angled between approximately zero and approximately fifteen degrees relative to a central longitudinal axis of the manifold.

20. The apparatus according to claim 17, wherein the channel is angled between approximately fifteen and approximately ninety degrees relative to a central longitudinal axis of the manifold.

* * * * *